United States Patent
Kobayashi et al.

(10) Patent No.: US 7,090,961 B2
(45) Date of Patent: Aug. 15, 2006

(54) PHOTO ACID GENERATOR, CHEMICAL AMPLIFICATION RESIST MATERIAL AND PATTERN FORMATION METHOD

(75) Inventors: Tomohiro Kobayashi, Niigata-ken (JP); Satoshi Watanabe, Niigata-ken (JP); Tsunehiro Nishi, Niigata-ken (JP); Youichi Ohsawa, Niigata-ken (JP); Katsuhiro Kobayashi, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/424,269

(22) Filed: Apr. 28, 2003

(65) Prior Publication Data

US 2003/0224290 A1 Dec. 4, 2003

(30) Foreign Application Priority Data

May 1, 2002 (JP) ............................. 2002-129559

(51) Int. Cl.
G03F 7/004 (2006.01)
G03F 7/039 (2006.01)
C07D 327/06 (2006.01)

(52) U.S. Cl. .................................. 430/270.1; 549/14
(58) Field of Classification Search .................. 549/14; 430/270.1

See application file for complete search history.

(56) References Cited

U.S. PATENT DOCUMENTS

| 5,585,507 A | 12/1996 | Nakano et al. ................. 556/7 |
| 5,635,332 A | 6/1997 | Nakano et al. ............. 430/270.1 |

(Continued)

FOREIGN PATENT DOCUMENTS

GB 2 102 421 * 2/1983

(Continued)

OTHER PUBLICATIONS

Oximes of dialkyl- and alkyleneacetonylsulfonium bromides. Krivenchuk, V. E. P.estits. Polim. Plast. Mass., Kiev, USSR Khimoko-Farmatsevticheskii Zhurnat (1970), 4(10), 18-22.*

(Continued)

*Primary Examiner*—Hoa Van Le
(74) *Attorney, Agent, or Firm*—Myers Bigel Sibley & Sajovec, PA

(57) ABSTRACT

A high resolution resist material comprising an acid generator is provided so that high sensitivity and high resolution for high energy rays of 300 nm or less, small line-edge roughness, and excellence in heat stability and storage stability are obtained. Moreover, a pattern formation method using this resist material are provided. Specifically, a novel compound of the following general formula (1); and a positive resist material comprising this compound preferably as a photo acid generator, and a base resin; are provided. This positive resist material may contain a basic compound or a dissolution inhibitor. Further, the present invention provides a pattern formation method comprising the steps of applying this positive resist material on a substrate, then heat-treating the material, exposing the treated material to a high energy ray having a wavelength of 300 nm or less via a photo mask, optionally heat-treating the exposed material, and developing the material using a developer.

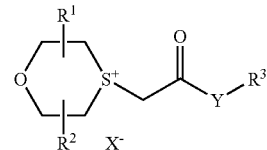

15 Claims, 2 Drawing Sheets

Si SUBSTRATE

U.S. PATENT DOCUMENTS

| | | | |
|---|---|---|---|
| 6,440,634 B1 | 8/2002 | Ohsawa et al. | 430/270.1 |
| 2004/0072097 A1* | 4/2004 | Kodama | 430/270.1 |

FOREIGN PATENT DOCUMENTS

| | | |
|---|---|---|
| JP | 8027102 | 1/1996 |
| JP | 10319581 | 12/1998 |
| JP | 2000-292917 | 10/2000 |

OTHER PUBLICATIONS

Abstract of US 20040072097 on pp. 2-5 of Search Report on Nov. 30, 2005.*

Azuma, T., et al. "Line edge roughness of chemically amplified resists." *Advances in Resist Technology and Processing XVII* 3999:264-269 (2000).

* cited by examiner

Si SUBSTRATE

PHOTO ACID GENERATOR, CHEMICAL AMPLIFICATION RESIST MATERIAL AND PATTERN FORMATION METHOD

RELATED APPLICATION

This application claims priority from Japanese Patent Application No. 2002-129559 filed May 1, 2002, the disclosure of which is incorporated by reference herein in its entirety.

BACKGROUND OF THE INVENTION

1. Field of the Invention

The present invention relates to an onium salt containing as a photo acid generator a specific thioxane skeleton at a cation moiety; a resist material for exposure to high energy rays having a wavelength preferably of 300 nm or less, containing this onium salt; and a pattern formation method using this resist material.

2. Description of the Related Art

Recently, with a higher degree of integration and higher speed of LSI, fine structure of a pattern rule is desired, and under such conditions, far ultraviolet lithography and vacuum ultraviolet lithography are regarded as promising as fine processing technologies of the next generation.

Currently, tip semiconductors of a 0.15 μm rule are produced by photolithography using a KrF excimer laser, and a 0.13 μm rule is also at the initial stages of production. Realization of photolithography using an ArF excimer laser ray as a light source is eagerly desired as a technology essential to ultra-fine processing of 0.13 μm or less.

Particularly, in photolithography using an ArF excimer laser ray as a light source, resist materials having high sensitivity capable of manifesting sufficient resolution with a small exposure amount, for preventing deterioration of precise and expensive optical materials has been demanded. As a device for realizing resist materials of high sensitivity, it is most common to select that which is highly transparent at a wavelength of 193 nm as each composition. For example, with respect to base resins, there are suggested poly(meth)acrylic acid and derivatives thereof, a norbornene-maleic anhydride alternating polymer, polynorbornene and metathesis ring-opened polymer, and the like, and effects of certain extent have been obtained from the standpoint of an increase in transparency of a resin single body. However, regarding the acid generator, when transparency increases, acid generation efficiency decreases, resulting in low sensitivity, or leading to deficiency in heat stability and storage stability, that is, those satisfying practical requirements are not obtained yet at present. (Meth) acrylic acid is an abbreviation for methacrylic acid and/or acrylic acid, therefore, poly(meth)acrylic acid means polymethacrylic acid and/or polyacrylic acid.

For example, alkylsulfonium salts suggested in Japanese Patent Provisional Publication Nos. 7-25846/1995 (U.S. Pat. Nos. 5,585,507 and 5,635,332), 7-28237/1995 (U.S. Pat. Nos. 5,585,507 and 5,635,332), 8-27102/1996 and 2000-292917, and the like have very high transparency, while, having insufficient acid generation efficiency and having difficulty also in heat stability. Thus, they are not satisfactory. Alkylarylsulfonium salts suggested in Japanese Patent Provisional Publication No. 10-319581/1998, and the like have good balance between transparency and acid generation efficiency and have high sensitivity, although deficient in heat stability and storage stability. The arylsulfonium salts which have been effective in photolithography using a KrF excimer laser ray are excellent in acid generation efficiency, heat stability and storage stability. However, they are remarkably low in transparency, and patterns after development are in the form of significant taper. Although there is a device for decreasing film thickness of a resist for compensating its transparency, this case leads to a remarkable decrease in the etching resistance of a resist film, namely, this device is not suitable as a pattern formation method. These are cases in which mainly the structure of the cation side of an onium salt is changed, and there is a report that the kind of acid generated and the kind of acid-labile group are in a tight relation, in resolution and pattern formation.

With promotion of fine structure, a difference in dimension among line-edge roughness, isolated pattern and dense pattern (I/G bias) is becoming problematic. It is conventionally well-known that even if dimensions on a mask are equivalent, a difference in dimensions occurs between the dense pattern and isolated pattern after development. In dimensions over the wavelength, the above-described problem is serious.

The reason for this is that optical strength varies depending on a difference in light interference in image formation of the dense pattern and isolated pattern. For example, FIG. 1 shows dimensions when the pitch of 0.18μ line is changed under optical conditions of a wavelength of 248 nm, NA of 0.6 and σ of 0.75. When standardized so that the line dimension is 0.18 μm at a pitch of 0.36 μm (0.18 μm line, 0.18 μm space), the dimensions of optical images once narrows and then broadens with expansion of pitch.

Next, results measuring the resist dimension after development are also shown. For the resist dimension, simulation software PROLITH 2 Ver. 6.0 available from KLA-Tencor Corporation (formerly, Finle Technologies Inc.) was used. The resist dimension narrows with expansion of pitch, further, narrows increasingly with an increase in acid diffusion. A problem of diffuseness/denseness dependency in which the dimensions of an isolated pattern narrow as compared with those of a dense pattern is becoming of great concern. It is understood from the above-described simulation results that a method of decreasing acid diffusion is effective as the method of decreasing diffuseness/denseness dependency. However, when the acid diffusion is too small, there occurs a problem that the side wall of a resist pattern after development becomes uneven and rough skin caused by standing wave, or line-edge roughness increases. For example, FIG. 2 shows the results of calculation of the cross-sectional form of a resist of an 0.18 μm line and space pattern on the Si substrate when the acid diffusion distance is varied using the above-described simulation software PROLITH Ver. 6.0 available from KLA-Tencor Corporation. It is shown that when the acid diffusion distance is smaller, unevenness of the side wall caused by standing wave is remarkable. Also regarding line-edge roughness observed from above SEM, the same tendency is shown, namely, when acid diffusion is smaller, line-edge roughness increases further. For decreasing the roughness of a line, it is common to increase acid diffusion distance. However, diffuseness/denseness dependency cannot be improved further by this. As the method of improving line-edge roughness, methods of improving light contrast are mentioned. For example, at the same exposure wavelength, when the dimension of line width is larger, line-edge roughness decreases. Even at the same exposure wavelength and the same dimension, when NA of a stepper is higher, smaller line-edge roughness is obtained in off-axis illumination (for example, annular illumination and quadrupole illumination) than in normal illumination, usually, on a phase shift mask than on a Cr mask. The contrast and line-edge roughness of line-edge of a pattern are correlated, and when line-edge contrast is steeper, line-edge roughness is smaller. Further, it is supposed that smaller line-edge roughness is obtained in the case of exposure to shorter wavelength. When line-edge roughness in KrF exposure and line-edge roughness in ArF exposure are compared, optical contrast is expected to be higher by shorter wavelength in ArF exposure, and line-edge roughness to be small. However, there is a report that KrF exposure is actually far superior (SPIE 3999, 264, (2000)). This is based on a difference in abilities of KrF resist materials and ArF resist materials, and indicates that, in particular, line-edge roughness derived from materials in the ArF exposure is of concern, and it is desired to obtain an acid generator that does not worsen diffuseness/denseness dependency while improving line-edge roughness, simultaneously.

Though 2-oxoethylarylthiacyclopentanium salt shown in the above-described Japanese Patent Provisional Publication No. 2000-292917 is suggested as that which is excellent in sensitivity and still further excellent in rectangularity of a resist pattern, it has been found that it is not satisfactory as an acid generator that does not worsen diffuseness/denseness dependency while improving line-edge roughness, simultaneously.

SUMMARY OF THE INVENTION

The present invention proposes an onium salt containing as a photo acid generator a specific thioxane skeleton at a cation moiety and application of this onium salt to a positive resist, and an object thereof is to provide (1) a high resolution resist material containing an acid generator compounded showing high sensitivity and high resolution for high energy rays of 300 nm or less, producing small line-edge roughness, and being excellent in heat stability and storage stability, and (2) a pattern formation method using this resist material.

The present inventors have intensively studied to achieve the above-described object, and resultantly found that an onium salt containing as a photo acid generator a specific thioxane skeleton at a cation moiety, namely, a sulfonium salt of the following general formula (1) shows high sensitivity for high energy rays preferably of 300 nm or less and has sufficient heat stability and storage stability, a chemical amplification positive resist material containing this compound has high resolution and is excellent in rectangularity, and this resist material is extremely effective for precise fine processing. It is supposed that an effect of improving line-edge roughness without worsening diffuseness/denseness dependency simultaneously is manifested since control of acid diffusion by an oxygen atom of the thioxane skeleton is effectively performed after generation of a photo acid.

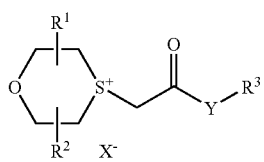
(1)

wherein $R^1$ and $R^2$ may be the same or different and each represents a hydrogen atom or a linear, branched or cyclic alkyl group having 1 to 8 carbon atoms, and Y represents a single bond or an oxygen atom, nitrogen atom or alkylene group having 1 to 4 carbon atoms; $R^3$ represents a linear, branched or cyclic alkyl group having 1 to 8 carbon atoms or an aryl group having 6 to 16 carbon atoms, and may be substituted by an alkyl group having 1 to 4 carbon atoms, a fluorinated alkyl group, alkoxy group or fluorinated alkoxy group, or a nitro group, cyano group, fluorine atom, phenyl group, substituted phenyl group, acetyl group or benzoyloxy group; and $X^-$ represents a non-nucleophilic counter ion having 1 to 20 carbon atoms.

Namely, the present invention provides a novel compound of the general formula (1), and a positive resist material comprising this photo acid generator and a base resin wherein this compound is used as a photo acid generator. This positive resist material may also comprise a basic compound and a dissolution inhibitor. Further, the present invention provides a pattern formation method comprising the steps of applying this positive resist material on a substrate, heat-treating the material, exposing the heat-treated material to a high energy ray having a wavelength of 300 nm or less via a photo mask, optionally heat-treating the exposed material, and subsequently performing development by a developing solution.

The resist material comprising the acid generator of the invention is excellent particularly in resolution, heat stability and storage stability, and also yields small line-edge roughness.

DETAILED DESCRIPTION OF THE PREFERRED EMBODIMENTS

Figure 1:
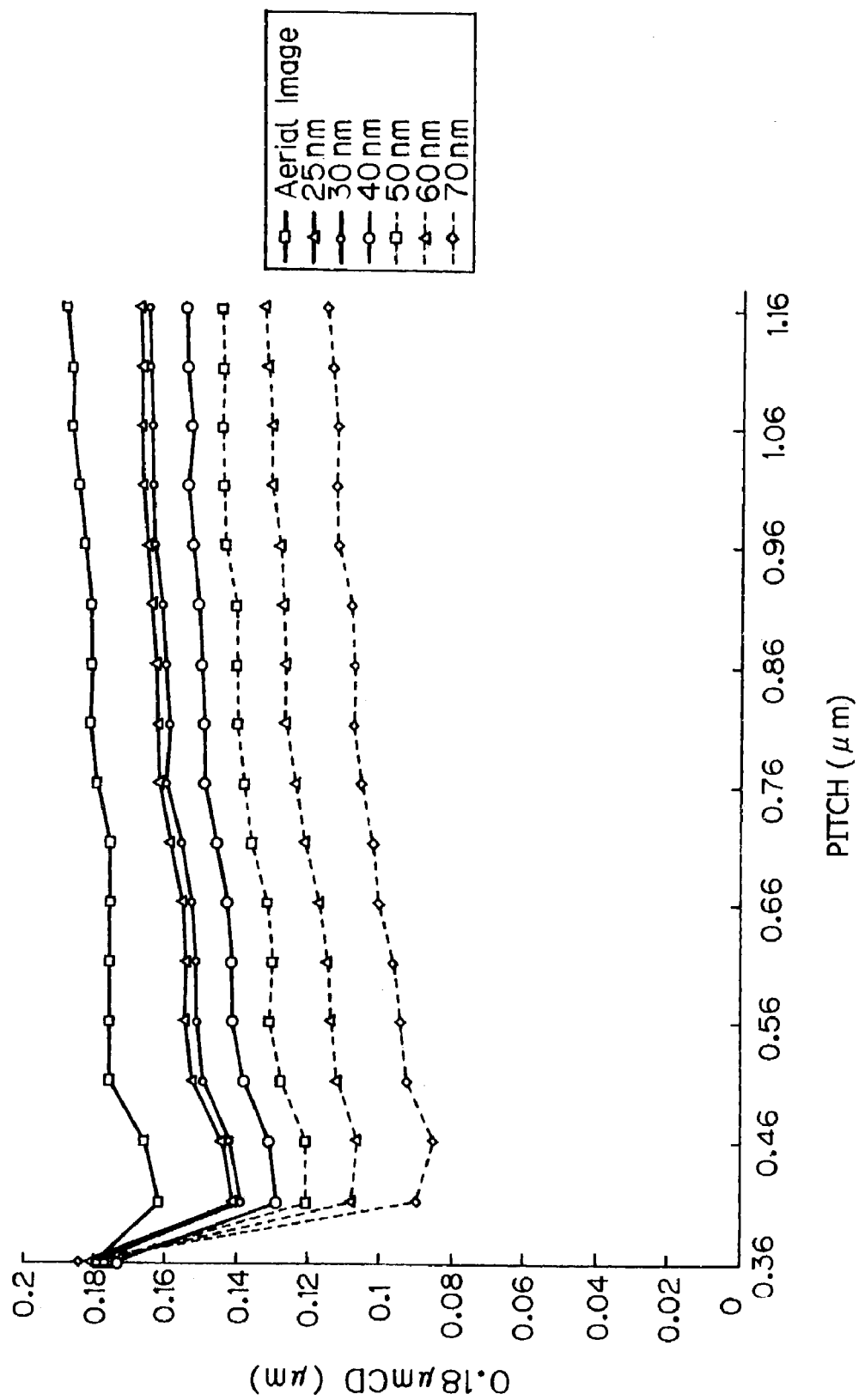
FIG. 1 shows results of simulation calculation showing change of line dimension when line pitch and acid diffusion distance are varied, and 25 to 70 nm are diffusion distance.
Figure 2:
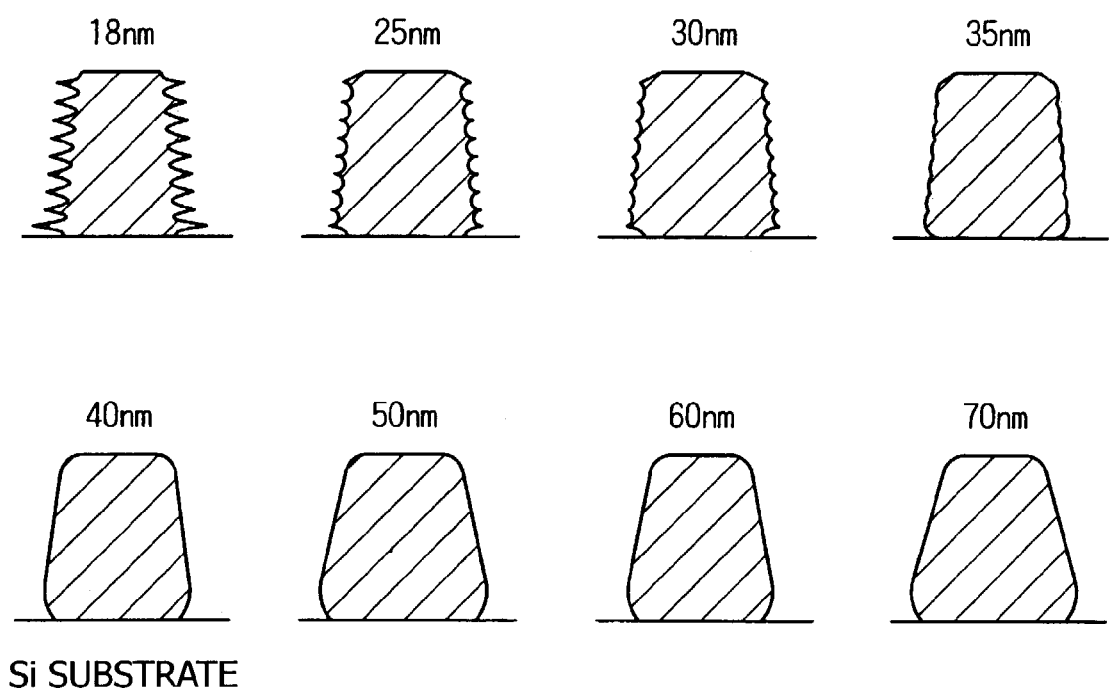
FIG. 2 shows results of simulation calculation of the sectional form of a resist when the acid diffusion distance is changed from 18 to 70 nm.

The present invention will be illustrated further in detail below.

The anion moiety in the general formula (1) is a non-nucleophilic counter ion having 1 to 20 carbon atoms. The non-nucleophilic counter ion is an ion being poor in nucleophilic reactivity and having high chemical stability, and includes fluoroalkylsulfonates such as triflate and nonafluorobutanesulfonate, arylsulfoantes such as tosylate and benzenesulfonate, and alkylsulfonates such as butanesulfonate.

In the general formula (1), it is preferable that both of $R^1$ and $R^2$ are a hydrogen atom. Further, in the general formula (1), it is preferable that $R^3$ is a phenyl group or naphthyl group.

By changing the combination of $R^1$, $R^2$, $R^3$ and Y, various combinations are possible. Although all of them cannot be shown, some examples for the cation moiety are below.

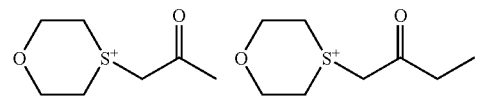

-continued

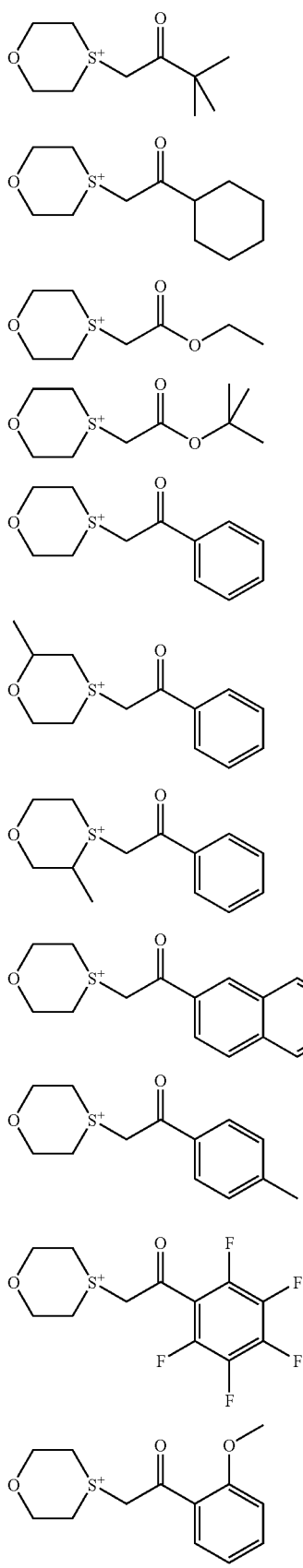

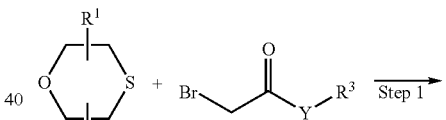

The method of synthesizing a sulfonium salt represented by the general formula (1) comprises, for example, a reaction of a thioxane compound with an acetyl bromide compound (Step 1) and an ion exchange reaction (Step 2). Although examples thereof are described below, the scope of the invention is not limited to these. In Step 1, nitromethane is used as a solvent, and stirring at room temperature is conducted for several hours before completion. The amount of a thiophene compound and the amount of an acetyl bromide compound are preferably in equimolar. The resulted compound 1 is washed with diethyl ether and water, and extracted into an aqueous phase. Next, a perfluoroimidic acid is added in equimolar to the compound 1, dichloromethane or chloroform is added to this, anion exchange is effected at room temperature for several minutes to dozens of minutes while stirring, and the final compound is extracted into an organic phase. The organic phase is concentrated, crystallized and purified from diethyl ether, to obtain the final compound.

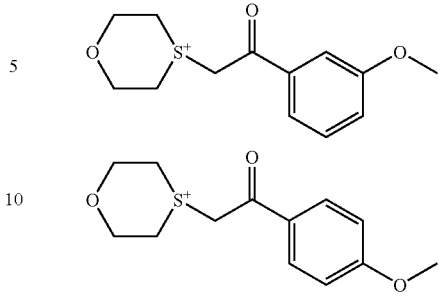

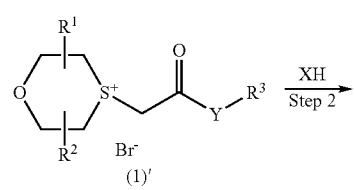

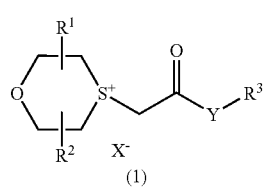

The preferable amount of an onium salt of the formula (1) is from 0.1 to 15 parts by weight, particularly from 0.5 to 10 parts by weight based on 100 parts by weight of a base resin. When the amount is too small, it may lead to low sensitivity, and when it is too high, transparency may lower and the resolving ability of a resist material may decrease.

The base resin which can be used in combination with the photo acid generator of the invention, includes one or more polymers selected from the group consisting of polyhydroxystyrene and derivative thereof; polyacrylic acid and derivative thereof; polymethacrylic acid and derivative thereof; copolymers formed by the monomers selected from hydroxystyrene, acrylic acid, methacrylic acid and derivative thereof; copolymers formed by three or more monomers selected from cycloolefins and derivative thereof, maleic anhydride, acrylic acid and derivative thereof; copolymers formed by three or more monomers selected from cycloolefins and derivative thereof, maleimide, acrylic acid and derivative thereof; polynorbornene; and metathesis polymers by ring-opening polymerization. The derivative here mean those containing the main skeleton before and after the derivation such that the acrylic acid derivative includes acrylate, the methacrylic acid derivative includes methacrylate, and the hydroxystyrene derivative includes alkoxystyrene.

The resin for the resist for a KrF excimer laser includes, but not limited to, polyhydroxystyrene (PHS), and copolymers formed by the monomers selected from hydroxystyrene, styrene, acrylate, methacrylate and maleimide-N-carboxylate. The resin for the resist for an ArF excimer laser includes, but not limited to, acrylates, methacrylates, alternating copolymers of norbornene with maleic anhydride, alternating copolymers of tetracyclododecene with maleic anhydride, polynorbornenes, and metathesis polymers by ring-opening polymerization.

In the case of a positive resist, it is common to lower the dissolution speed of non-exposed portions by substituting a hydroxyl group of phenol or carboxyl group with an acid-labile group. That is, the base regain with a hydrogen atom of a carboxyl group or a hydrogen atom of a phenolic hydroxyl group being substituted with an acid-labile group having an alkali dissolution controlling ability can be used. Because the acid-labile group is dissociated by the action of an acid generated in exposure, the base resin increases solubility into an alkali aqueous solution. Thus, the resin can be comprised in a positive resist material.

The acid-labile group in the base resin is selected variously, and it is preferable that the group is particularly a group of the following formula (AL10), (AL11), a tertiary alkyl group having 4 to 40 carbon atoms of the following formula (AL12), a trialkylsilyl group having 1 to 6 carbon atoms, an oxoalkyl group having 4 to 20 carbon atoms, or the like.

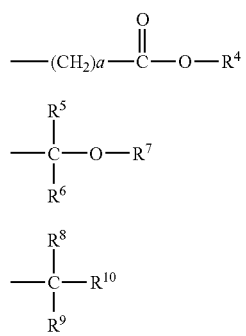

In the formulae (AL10) and (AL11), $R^4$ and $R^7$ each represents a linear, branched or cyclic alkyl group having 1 to 20 carbon atoms, and may contain a hetero atom such as oxygen, sulfur, nitrogen or fluorine.

$R^5$ and R6 each represents a linear, branched or cyclic alkyl group having 1 to 20 carbon atoms, and may contain a hetero atom such as oxygen, sulfur, nitrogen or fluorine, and "a" represents an integer of 0 to 10. $R^5$ and $R^6$, $R^5$ and $R^7$, or $R^6$ and $R^7$ may be bonded respectively to form a ring.

$R^8$, $R^9$ and $R^{10}$ each represents a linear, branched or cyclic alkyl group having 1 to 20 carbon atoms, and may contain a hetero atom such as oxygen, sulfur, nitrogen or fluorine. $R^8$ and $R^9$, $R^8$ and $R^{10}$, or $R^9$ and $R^{10}$ may be bonded respectively to form a ring.

Specific examples of the formula (AL10) include a tert-butoxycarbonyl group, tert-butoxycarbonylmethyl group, tert-amyloxycarbonyl group, tert-amyloxycarbonylmethyl group, 1-ethoxyethoxycarbonylmethyl group, 2-tetrahydropyranyloxycarbonylmethyl group, and 2-tetrahydropyranyloxycarbonylmethyl group, and substituents of the following general formulae (AL10)-1 to (AL10)-10.

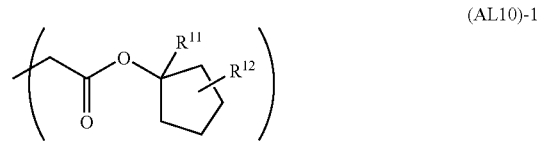

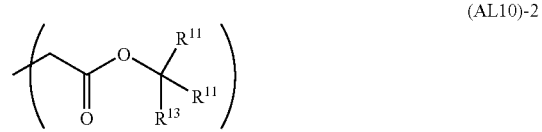

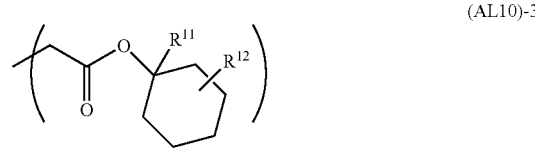

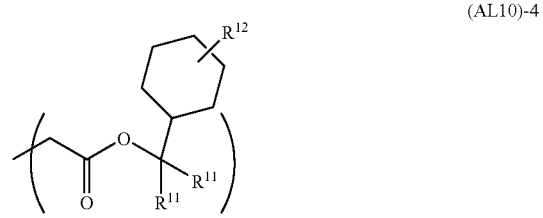

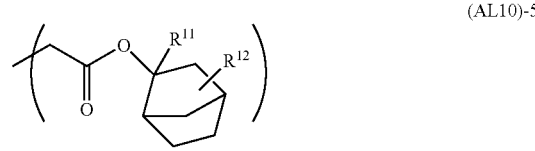

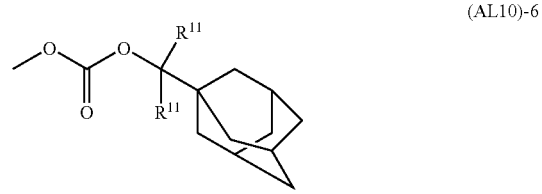

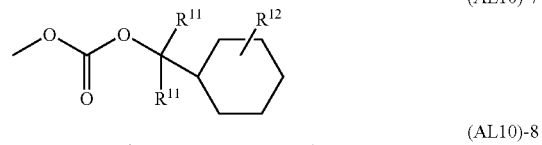

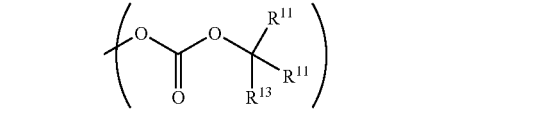

-continued (AL10)-10

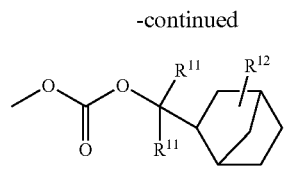

In the formulae (AL10)-1 to (AL10)-10, $R^{11}$ may be same or different and represents a linear, branched or cyclic alkyl group having 1 to 8 carbon atoms, or an aryl or aralkyl group having 6 to 20 carbon atoms. $R^{12}$ and $R^{14}$ each is not present or represents a linear, branched or cyclic alkyl group having 1 to 20 carbon atoms. $R^{13}$ represents an aryl or aralkyl group having 6 to 20 carbon atoms.

The acetal compounds of the formula (AL11) include the following (AL11)-1 to (AL11)-23.

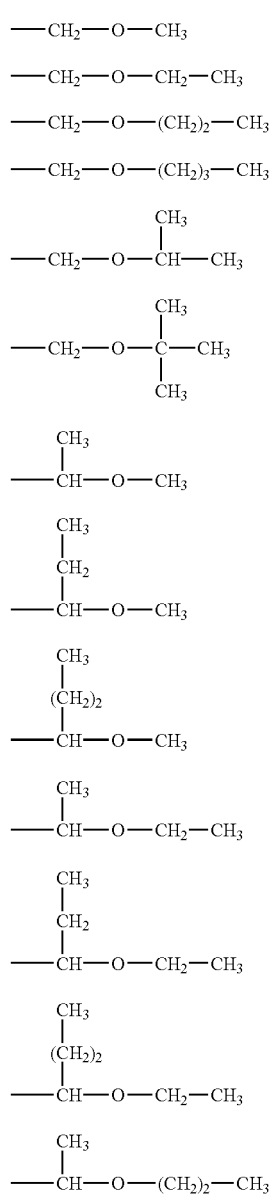

(AL11)-1
(AL11)-2
(AL11)-3
(AL11)-4
(AL11)-5
(AL11)-6
(AL11)-7
(AL11)-8
(AL11)-9
(AL11)-10
(AL11)-11
(AL11)-12
(AL11)-13

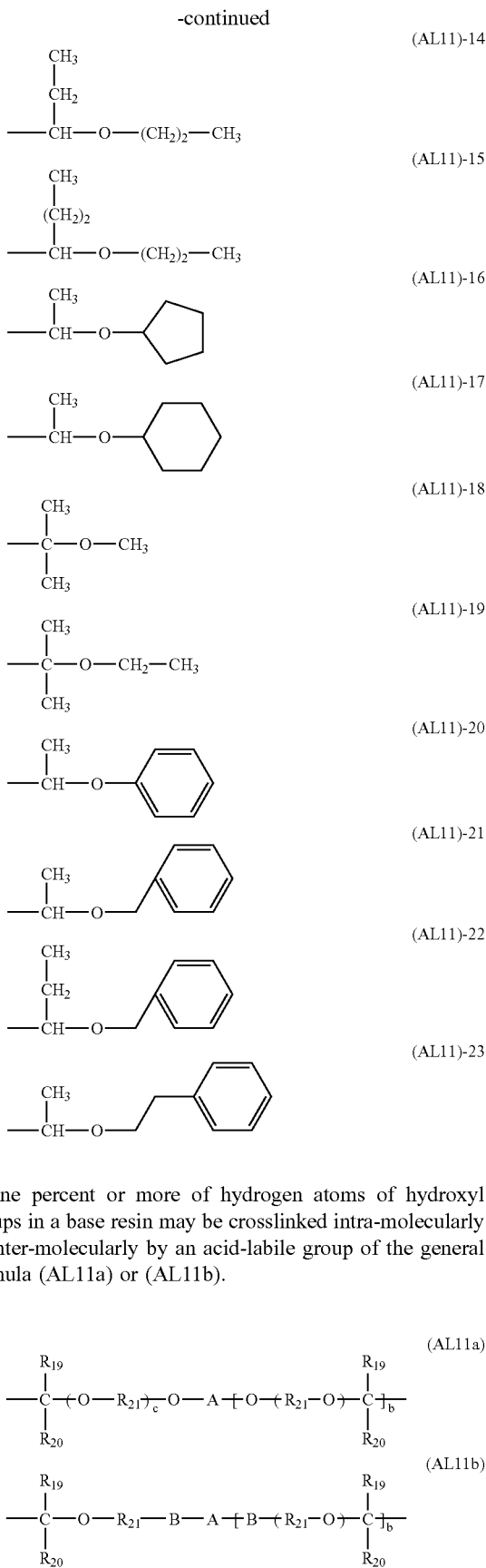

(AL11)-14
(AL11)-15
(AL11)-16
(AL11)-17
(AL11)-18
(AL11)-19
(AL11)-20
(AL11)-21
(AL11)-22
(AL11)-23

One percent or more of hydrogen atoms of hydroxyl groups in a base resin may be crosslinked intra-molecularly or inter-molecularly by an acid-labile group of the general formula (AL11a) or (AL11b).

In the formulae, $R^{19}$ and $R^{20}$ represents a linear, branched or cyclic alkyl group having 1 to 8 carbon atoms. $R^{19}$ and $R^{20}$ may be bonded to form a ring, and when the ring is formed, $R^{19}$ and $R^{20}$ each represents a linear or branched alkylene group having 1 to 8 carbon atoms. $R^{21}$ represents a linear, branched or cyclic alkylene group having 1 to 10 carbon atoms, and c represents an integer of 0 to 10. The A represents a (b+1)-valent aliphatic or alicyclic saturated hydrocarbon group having 1 to 50 carbon atoms, an aromatic hydrocarbon group or heterocyclic group, and these groups may contain an intervening hetero atom, or a part of hydrogen atoms bonded to the carbon atoms may be substituted by a hydroxyl group, carboxyl group, carbonyl group or fluorine atom. The B represents —CO—O—, —NHCO—O— or —NHCONH—. The b independently represents an integer of 1 to 7.

The crosslinked acetal of the general formulae (AL11-a) and (AL11-b) include the following (AL11)-24 to (AL11)-31.

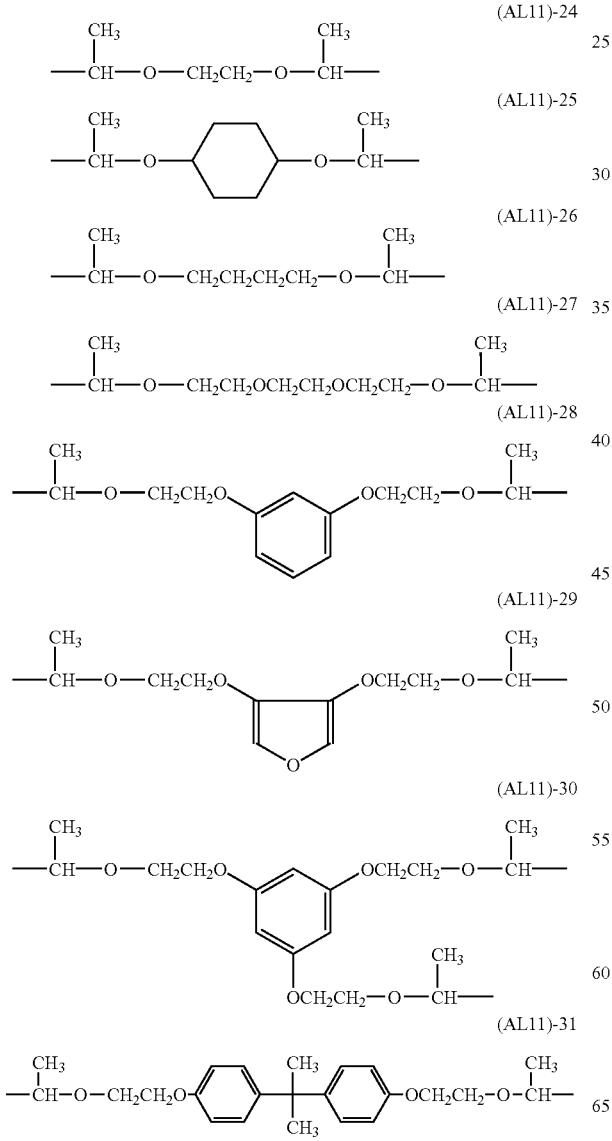

The tertiary alkyl group of the formula (AL12) includes a tert-butyl group, triethylcarbyl group, 1-ethylnorbonyl group, 1-methylcyclohexyl group, 1-ethylcyclopentyl group, 2-(2-methyl)adamantyl group, 2-(2-ethyl)adamantyl group, tert-amyl group, and the following general formulae (AL12)-1 to (AL12)-18.

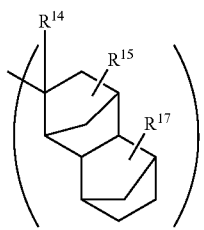 (AL12)-9

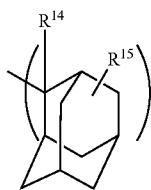 (AL12)-10

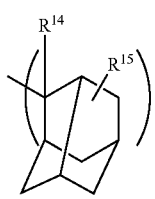 (AL12)-11

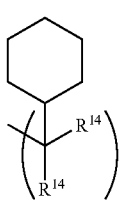 (AL12)-12

 (AL12)-13

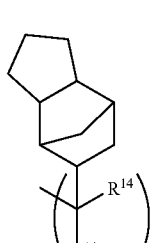 (AL12)-14

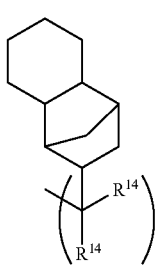 (AL12)-15

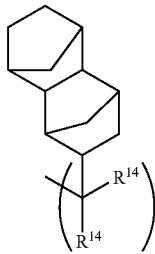 (AL12)-16

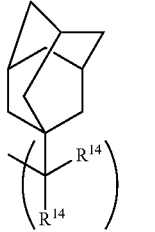 (AL12)-17

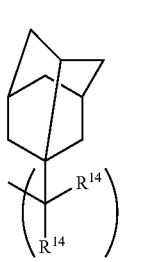 (AL12)-18

In the formulae, $R^{14}$ may be same or different and represents a linear, branched or cyclic alkyl group having 1 to 8 carbon atoms, or an aryl or aralkyl group having 6 to 20 carbon atoms. $R^{15}$ and $R^{17}$ each is not present or represents a linear, branched or cyclic alkyl group having 1 to 20 carbon atoms. $R^{16}$ represents an aryl or aralkyl group having 6 to 20 carbon atoms.

Further, as shown in (AL12)-19 to (AL12)-20, polymers may be crosslinked intra-molecularly or inter-molecularly including $R^{18}$ which is a di- or more-valent alkylene or arylene group. $R^{14}$ in (AL12)-19 is defined above, and $R^{18}$ represents a linear, branched or cyclic alkylene group having 1 to 20 carbon atoms, or an arylene group, and may contain a hetero atom such as an oxygen atom, sulfur atom or nitrogen atom. The d represents an integer of 1 to 3.

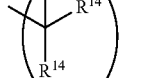 (AL12)-19

(AL12)-20

Further, $R^{14}$, $R^{15}$, $R^{16}$ and $R^{17}$ each may contain a hetero atom such as oxygen, nitrogen or sulfur, and includes the following (13)-1 to (13)-7.

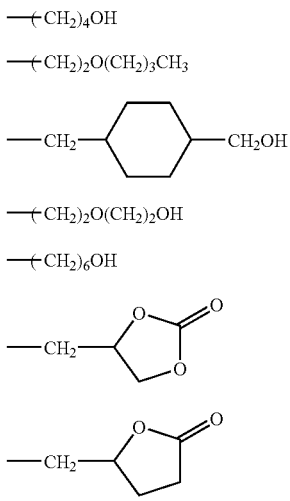

(13)-1 —(CH₂)₄OH
(13)-2 —(CH₂)₂O(CH₂)₃CH₃
(13)-3 —CH₂—⟨cyclohexyl⟩—CH₂OH
(13)-4 —(CH₂)₂O(CH₂)₂OH
(13)-5 —(CH₂)₆OH
(13)-6 —CH₂—(cyclic carbonate)
(13)-7 —CH₂—(γ-butyrolactone)

The base resin used in the present invention may be a base resin of a polymer structure containing a silicon atom. The silicon-containing polymer includes polymers containing silicon as an acid-labile group at first. The acid-labile group containing silicon includes a trialkylsilyl group having 1 to 6 carbon atoms. The specific examples thereof include a trimethylsilyl group, triethylsilyl group and dimethyl-tert-butylsilyl group.

Further, the silicon-containing acid-labile groups below can be used.

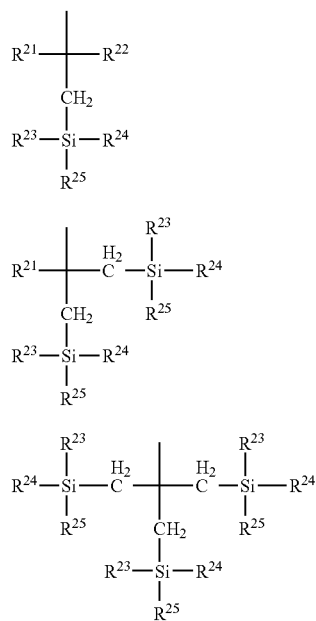

In the formulae, $R^{21}$ and $R^{22}$ each represents a hydrogen atom or an alkyl group having 1 to 20 carbon atoms. $R^{23}$, $R^{24}$ and $R^{25}$ may be same or different and each represents an alkyl or haloalkyl group having 1 to 20 carbon atoms, aryl group having 6 to 20 carbon atoms, or silicon-containing group bonded to a silicon atom in the formula by a siloxane or silethylene bond. $R^{21}$ and $R^{22}$ may be bonded to form a ring.

Specific examples of (A-4) include the below.

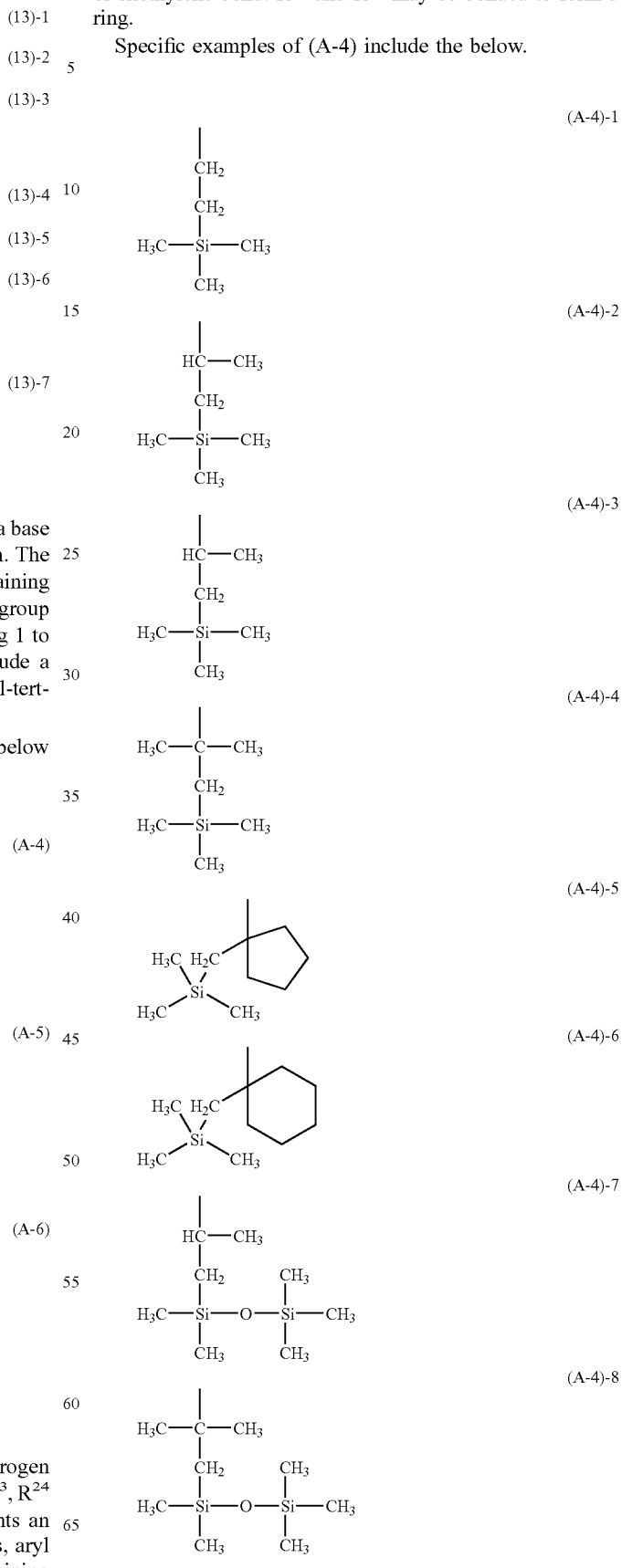

-continued

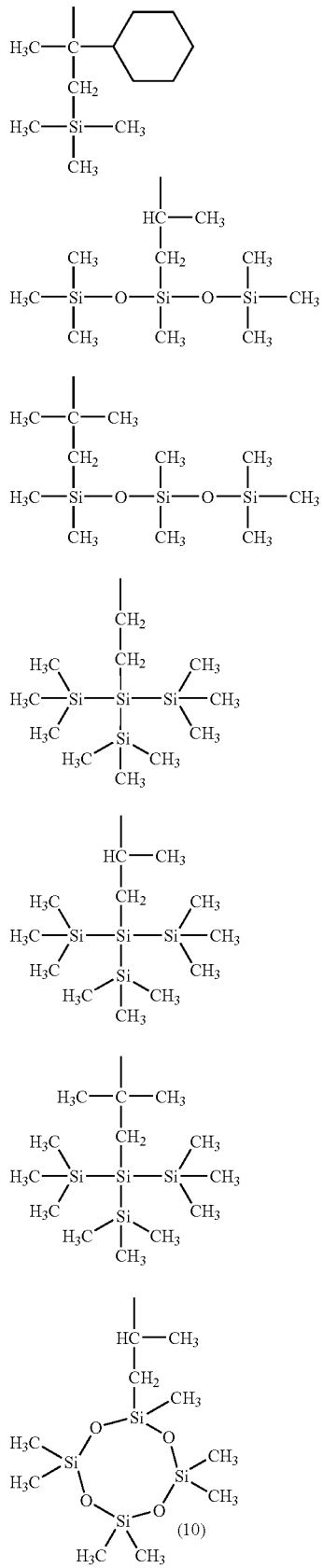

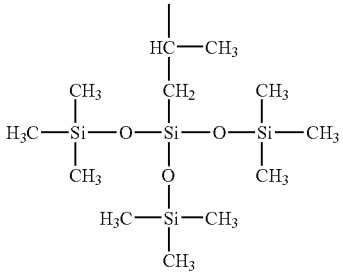

Further, cyclic silicon-containing acid-labile groups of the general formula (A-7) or (A-8) can also be used.

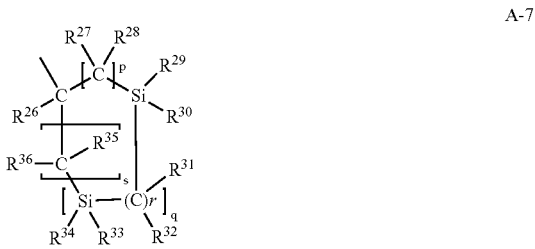

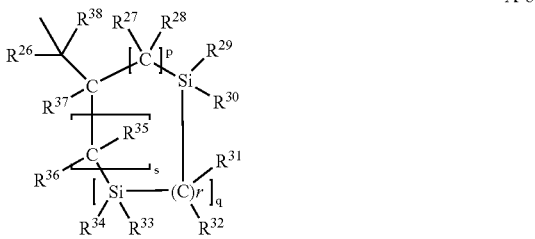

In the formulae, $R^{26}$ and $R^{38}$ each independently represents a linear, branched or cyclic alkyl group having 1 to 20 carbon atoms. $R^{27}$, $R^{28}$, $R^{31}$, $R^{32}$, $R^{35}$, $R^{36}$ and $R^{37}$ each independently represents a hydrogen atom or a linear, branched or cyclic alkyl group having 1 to 20 carbon atoms. $R^{29}$, $R^{30}$, $R^{31}$ and $R^{34}$ each independently represents a hydrogen atom or a linear, branched or cyclic alkyl group having 1 to 20 carbon-atom, fluorinated alkyl group having 1 to 20 carbon atoms, aryl group having 6 to 20 carbon atoms. The p, q, r and s each represents an integer of 0 to 10, satisfying $1 \leq p+q+s \leq 20$.

Specific examples of (A-7) and (A-8) includes the following.

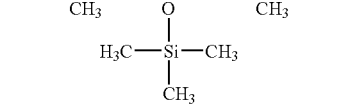

-continued

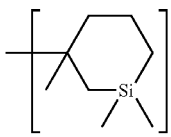
(A-7)-3

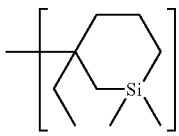
(A-7)-4

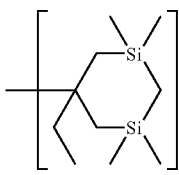
(A-7)-5

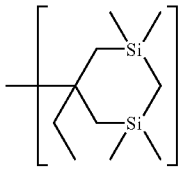
(A-7)-6

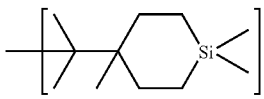
(A-8)-1

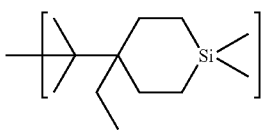
(A-8)-2

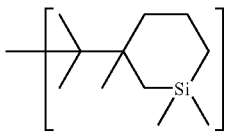
(A-8)-3

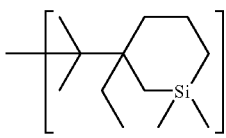
(A-8)-4

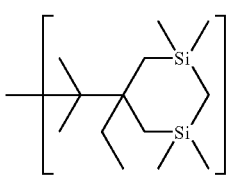
(A-8)-5

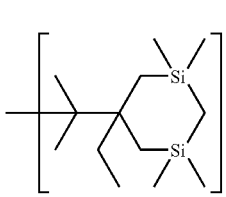
(A-8)-6

The trialkylsilyl group having 1 to 6 carbon atoms as an acid-labile group, includes a trimethylsilyl group, triethylsilyl group and dimethyl-tert-butylsilyl group.

As the silicon-containing polymer, silicon-containing repeating units stable to an acid can also be used.

The silicon-containing repeating units stable to an acid are shown in the following (9)-1 to 5.

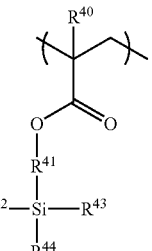
(9)-1

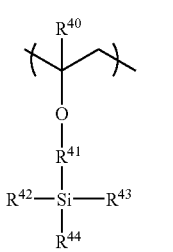
(9)-2

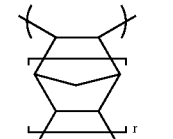
(9)-3

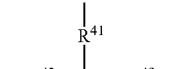
(9)-4

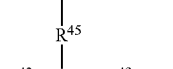
(9)-5

In the formula, $R^{40}$ represents a hydrogen atom, methyl group, fluorine atom or trifluoromethyl group. $R^{41}$ represents a divalent hydrocarbon group having 3 to 10 carbon atoms. $R^{42}$, $R^{43}$ and $R^{44}$ may be same or different and each represents a hydrogen atom, alkyl group having 1 to 10 carbon atoms, aryl group, alkyl group containing a fluorine atom, hydrocarbon group containing a silicon atom, or a group containing a siloxane bond. $R^{42}$ and $R^{43}$, $R^{43}$ and $R^{44}$, and $R^{42}$ and $R^{44}$ may be respectively bonded to form a ring. $R^{45}$ represents a single bond or alkylene group having 1 to 4 carbon atoms. The r is 0 or 1.

The more specific examples of (9)-5 include the following (10)-1 to 20.

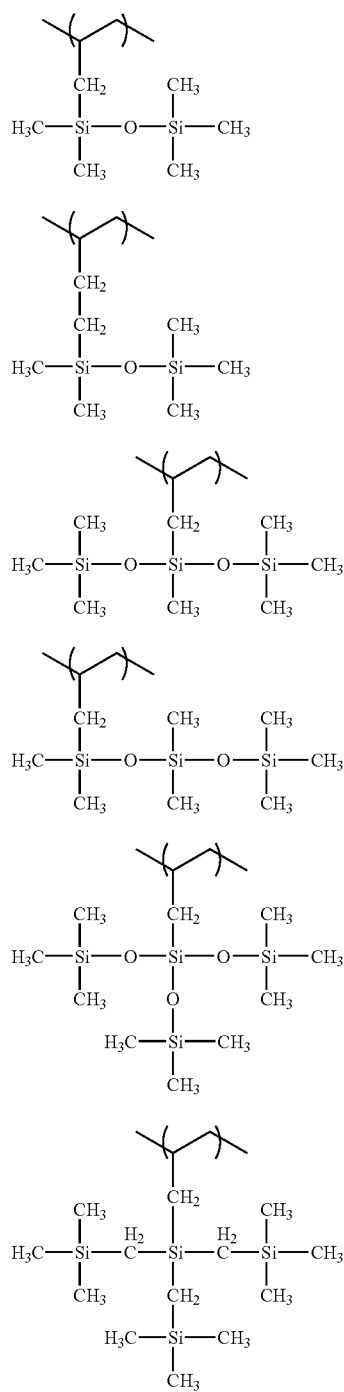

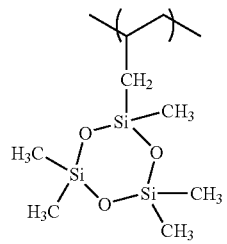
(10)-7

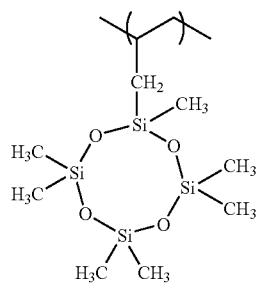
(10)-8

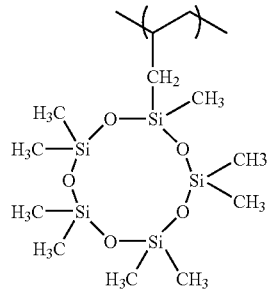
(10)-9

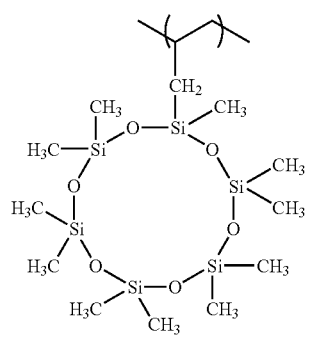
(10)-10

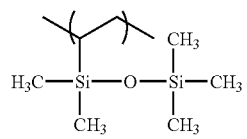
(10)-11

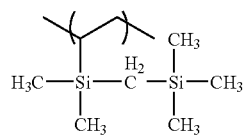
(10)-12

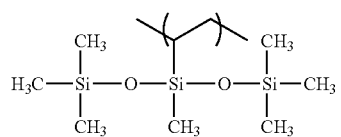
(10)-13

-continued (10)-14
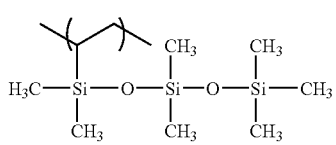

(10)-15
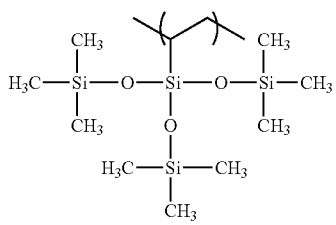

(10)-16
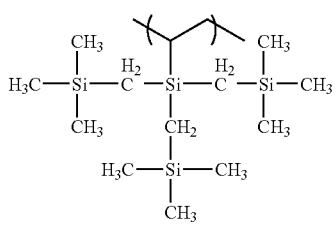

(10)-17
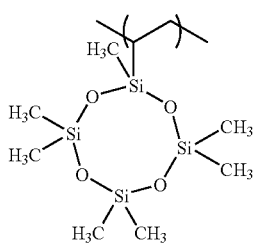

(10)-18
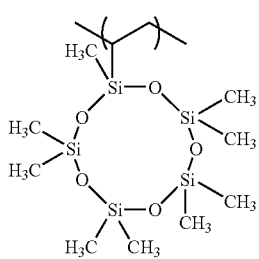

(10)-19
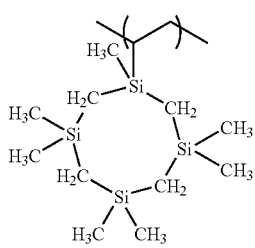

-continued (10)-20
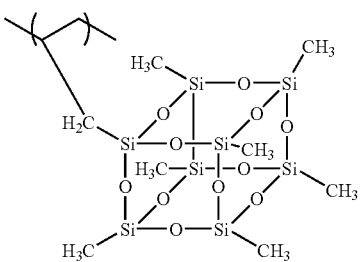

The above-described polymer compounds can be added not only singly but also in combination of two or more. The combination of polymer compounds can control the properties of a resist material. A plurality of polymer compounds having different molecular weights and degrees of dispersion can also be used.

The resist material of the invention may comprise a conventionally suggested acid generator different from the photo acid generator of the formula (1).

The compound as the acid generator includes:

i. onium salts of the following general formula (P1a-1), (P1a-2) or (P1b), ii. a diazomethane derivative of the following general formula (P2), iii. a glyoxime derivative of the following general formula (P3), iv. a bissulfone derivative of the following general formula (P4), v. sulfonates of N-hydroxyimide compounds of the following general formula (P5), vi. a β-ketosulfonic acid derivative, vii. a disulfone derivative, viii. a nitrobenzyl sulfonate derivative, ix. a sulfonate derivative.

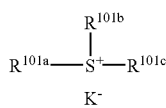

P1a-1

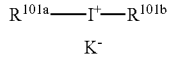

P1a-2 wherein $R^{101a}$, $R^{101b}$ and $R^{101c}$ each represents a linear, branched or cyclic alkyl group, alkenyl group, oxoalkyl group or oxoalkenyl group having 1 to 12 carbon atoms, aryl group having 6 to 20 carbon atoms, aralkyl or aryloxoalkyl group having 7 to 12 carbon atoms, and a part or all of hydrogen atoms in these groups may be substituted by an alkoxy group or the like; $R^{101b}$ and $R^{101c}$ may form a ring, and when the ring is formed, $R^{101b}$ and $R^{101c}$ each represents an alkylene group having 1 to 6 carbon atoms; $K^-$ represents a non-nucleophilic counter ion.

The $R^{101a}$, $R^{101b}$ and $R^{101c}$ may be the same or different, and each includes an alkyl group such as a methyl group, ethyl group, propyl group, isopropyl group, n-butyl group, sec-butyl group, tert-butyl group, pentyl group, hexyl group, heptyl group, octyl group, cyclopentyl group, cyclohexyl group, cycloheptyl group, cyclopropylmethyl group, 4-methylcyclohexyl group, cyclohexylmethyl group, norbornyl group and adamantyl group; an alkenyl group such as a vinyl group, allyl group, propenyl group, butenyl group, hexenyl group and cyclohexenyl group; an oxoalkyl group such as a 2-oxocyclopentyl group, 2-oxocyclohexyl group, 2-oxopropyl group, 2-cyclopentyl-2-oxoethyl group, 2-cyclohexyl-2-oxoethyl group and 2-(4-methylcyclohexyl)-2-oxoethyl group; an aryl group such as a phenyl group, naphthyl group, an alkoxyphenyl group including as a p-methoxyphenyl group, m-methoxyphenyl group, o-methoxyphenyl group, ethoxyphenyl group, p-tert-butoxyphenyl group and m-tert-butoxyphenyl group, an alkylphenyl group including a 2-methylphenyl group, 3-methylphenyl group, 4-methylphenyl group, ethylphenyl group, 4-tert-butylphenyl group, 4-butylphenyl group and dimethylphenyl group, an alkylnaphthyl group including a methylnaphthyl group and ethylnaphthyl group, an alkoxynaphthyl group including a methoxynaphthyl group and ethoxynaphthyl group, a dialkylnaphthyl group including a dimethylnaphthyl group and diethylnaphthyl, a dialkoxynaphthyl group including a dimethoxynaphthyl group and diethoxynaphthyl group; an aralkyl group such as a benzyl group, phenylethyl group and phenetyl group; an aryloxoalkyl group such as 2-aryl-2-oxyethyl groups including a 2-phenyl-2-oxoethyl group, 2-(1-naphthyl)-2-oxoethyl group and 2-(2-naphthyl)-2-oxoetyl group.

The non-nucleophilic counter ion $K^-$ includes a halide ion such as a chloride ion and bromide ion; fluoroalkylsulfonate such as triflate, 1,1,1-trifluoroethanesulfonate and nonafluorobutanesulfonate; arylsulfonate such as tosylate, benzenesulfonate, 4-fluorobenzenesulfonate and 1,2,3,4,5-pentafluorobenzenesulfonate; alkylsulfonate such as mesylate and butanesulfonate.

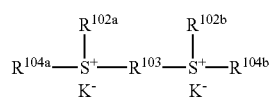

P1b wherein $R^{102a}$ and $R^{102b}$ each represents a linear, branched or cyclic alkyl group having 1 to 8 carbon atoms; $R^{103}$ represents a linear, branched or cyclic alkylene group having 1 to 10 carbon atoms; $R^{104a}$ and $R^{104b}$ each represents a 2-oxoalkyl group having 3 to 7 carbon atoms; $K^-$ represents a non-nucleophilic counter ion.

The $R^{102a}$ and $R^{102b}$ include a methyl group, ethyl group, propyl group, isopropyl group, n-butyl group, sec-butyl group, tert-butyl group, pentyl group, hexyl group, heptyl group, octyl group, cyclopentyl group, cyclohexyl group, cyclopropylmethyl group, 4-methylcyclohexyl group and cyclohexylmethyl group. $R^{103}$ includes a methylene group, ethylene group, propylene group, butylene group, pentylene group, hexylene group, heptylene group, octylene group, nonylene group, 1,4-cyclohexylene group, 1,2-cyclohexylene group, 1,3-cyclopentylene group, 1,4-cyclooctylene group and 1,4-cyclohexanedimethylene group. $R^{104a}$ and $R^{104b}$ include a 2-oxopropyl group, 2-oxocyclopentyl group, 2-oxocyclohexyl group and 2-oxocycloheptyl group. $K^-$ includes the same groups as those described for the formulae (P1a-1) and (P1a-2).

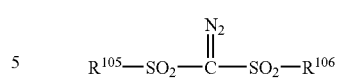

P2 wherein $R^{105}$ and $R^{106}$ each represents a linear, branched or cyclic alkyl group or halogenated alkyl group having 1 to 12 carbon atoms, aryl group or halogenated aryl group having 6 to 20 carbon atoms, or aralkyl group having 7 to 12 carbon atoms.

The alkyl group of $R^{105}$ and $R^{106}$ includes a methyl group, ethyl group, propyl group, isopropyl group, n-butyl group, sec-butyl group, tert-butyl group, pentyl group, hexyl group, heptyl group, octyl group, amyl group, cyclopentyl group, cyclohexyl group, cycloheptyl group, norbornyl group and adamantyl group. The halogenated alkyl group includes a trifluoromethyl group, 1,1,1-trifluoroethyl group, 1,1,1-trichloroethyl group and nonafluorobutyl group. The aryl group includes a phenyl group; alkoxyphenyl groups such as a p-methoxyphenyl group, m-methoxyphenyl group, o-methoxyphenyl group, ethoxyphenyl group, p-tert-butoxyphenyl group and m-tert-butoxyphenyl group; and alkylphenyl groups such as a 2-methylphenyl group, 3-methylphenyl group, 4-methylphenyl group, ethylphenyl group, 4-tert-butylphenyl group, 4-butylphenyl group and dimethylphenyl group. The halogenated aryl group includes a fluorophenyl group, chlorophenyl group and 1,2,3,4,5-pentafluorophenyl group. The aralkyl group includes a benzyl group and phenetyl group.

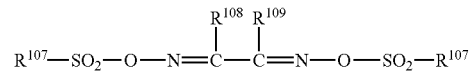

P3 wherein $R^{107}$, $R^{108}$ and $R^{109}$ each represents a linear, branched or cyclic alkyl group or halogenated alkyl group having 1 to 12 carbon atoms, an aryl group or halogenated aryl group having 6 to 20 carbon atoms, or aralkyl group having 7 to 12 carbon atoms. $R^{108}$ and $R^{109}$ may be mutually bonded to form a ring, and when the ring is formed, $R^{108}$ and $R^{109}$ each represents a linear or branched alkylene group having 1 to 6 carbon atoms.

The alkyl group, halogenated alkyl group, aryl group, halogenated aryl group and aralkyl group of $R^{107}$, $R^{108}$ or $R^{109}$ include the same specific groups as described for $R^{105}$ and $R^{106}$. The alkylene group of $R^{108}$ and $R^{109}$ includes a methylene group, ethylene group, propylene group, butylene group and hexylene group.

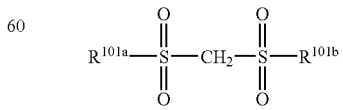

P4 wherein $R^{101a}$ and $R^{101b}$ are the same as those described above.

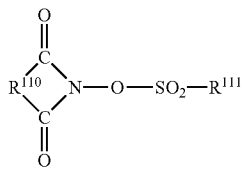

P5 wherein $R^{110}$ represents an arylene group having 6 to 10 carbon atoms, an alkylene group having 1 to 6 carbon atoms or an alkenylene group having 2 to 6 carbon atoms, and a part or all of the hydrogen atoms in these groups may be further substituted by a linear or branched alkyl group or alkoxy group having 1 to 4 carbon atoms, nitro group, acetyl group or phenyl group; $R^{111}$ represents a linear, branched or substituted alkyl group, alkenyl group or alkoxyalkyl group having 1 to 8 carbon atoms; phenyl group; or naphthyl group wherein a part or all of the hydrogen atoms in these groups may be further substituted by an alkyl group or alkoxy group having 1 to 4 carbon atoms; a phenyl group optionally substituted by an alkyl or alkoxy group having 1 to 4 carbon atoms; a phenyl group which may be substituted by an alkyl or alkoxy group having 1 to 4 carbon atoms, nitro group or acetyl group; a hetero aromatic group having 3 to 5 carbon atoms; or a chlorine atom or a fluorine atom.

Here, $R^{110}$ includes an arylene group such as a 1,2-phenylene group and 1,8-naphthylene group; an alkylene group such as a methylene group, 1,2-ethylene group, 1,3-propylene group, 1,4-butylene group, 1-phenyl-1,2-ethylene group and norbornane-2,3-diyl group; an alkenylene group such as a 1,2-vinylene group, 1-phenyl-1,2-vinylene group and 5-norboenen-2,3-diyl group. $R^{111}$ includes an alkyl group such as the same groups as described for $R^{101a}$, $R^{101b}$ and $R^{101c}$, an alkenyl group such as a vinyl group, 1-propenyl group, allyl group, 1-butenyl group, 3-butenyl group, isoprenyl group, 1-pentenyl group, 3-pentenyl group, 4-pentenyl group, dimethylallyl group, 1-hexenyl group, 3-hexenyl group, 5-hexenyl group, 1-heptenyl group, 3-heptenyl group, 6-heptenyl group and 7-octenyl group; and an alkoxyalkyl group such as methoxymethyl group, ethoxyethyl group, propoxymethyl group, butoxymethyl group, pentyloxymethyl group, hexyloxymethyl group, heptyloxymethyl group, methoxyethyl group, ethoxyethyl group, propoxyethyl group, butoxyethyl group, pentyloxyethyl group, hexyloxyethyl group, methoxypropyl group, ethoxypropyl group, propoxypropyl group, butoxypropyl group, methoxybutyl group, ethoxybutyl group, propoxybutyl group, methoxypentyl group, ethoxypentyl group, methoxyhexyl group and methoxyheptyl group.

The alkyl group having 1 to 4 carbon atoms which may further substituted, includes a methyl group, ethyl group, propyl group, isopropyl group, n-butyl group, isobutyl group and tert-butyl group. The alkoxy group having 1 to 4 carbon atoms includes a methoxy group, ethoxy group, propoxy group, isopropoxy group, n-butoxy group, isobutoxy group and tert-butoxy group. The phenyl group which may be substituted by an alkyl or alkoxy group having 1 to 4 carbon atoms, nitro group or acetyl group, includes a phenyl group, tolyl group, p-tert-butoxyphenyl group, p-acetylphenyl group and p-nitrophenyl group. The hetero aromatic group having 3 to 5 carbon atoms includes a pyridyl group and furyl group.

specifically, examples of the onium salts include diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl) sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethanesulfonate, (2-norbonyl)methyl(2-oxocyclohexyl)sulfonium trifluoromethanesulfonate, ethylenebis[methyl(2-oxocyclopentyl)sulfonium trifluoromethasulfonate], and 1,2'-naphthylcarbonylmethyltetrahydrothiophenyum triflate.

Examples of the diazomethane derivative include bis(benzenesulfonyl)diazomethane, bis(p-toluenesulfonyl)diazomethane, bis(xylenesulfonyl)diazomethane, bis(cyclohexylsulfonyl)diazomethane, bis(cyclopentylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfony-1-(tert-amylsulfonyl)diazomethane and 1-tert-amylsulfonyl-1-(tert-butylsulfonyl)diazomethane.

Examples of the glyoxime derivative include bis-o-(p-toluenesulfonyl)-α-dimethyl glyoxime, bis-O-(p-toluenesulfonyl)-α-diphenyl glyoxime, bis-O-(p-toluenesulfonyl)-α-dicyclohexyl glyoxime, bis-O-(p-toluenesulfonyl)-2,3-pentanedione glyoxime, bis-O-(p-toluenesulfonyl)-2-methyl-3,4-pentanedione glyoxime, bis-O-(n-butanesulfonyl)-α-dimethyl glyoxime, bis-O-(n-butanesulfonyl)-α-diphenyl glyoxime, bis-O-(n-butanesulfonyl)-α-dicyclohexyl glyoxime, bis-O-(n-butanesulfonyl)-2,3-pentanedione glyoxime, bis-O-(n-butanesulfonyl)-2-methyl-3,4-pentanedione glyoxime, bis-O-(n-methanesulfonyl)-α-dimethyl glyoxime, bis-O-(trifluoromethanesulfonyl)-α-dimethyl glyoxime, bis-O-(1,1,1-trifluoroethanesulfonyl)-α-dimethyl glyoxime, bis-O-(tert-butanesulfonyl)-α-dimethyl glyoxime, bis-O-(perfluorooctanesulfonyl)-α-dimethyl glyoxime, bis-O-(cyclohexanesulfonyl)-α-dimethyl glyoxime, bis-O-(benzenesulfonyl)-α-dimethyl glyoxime, bis-O-(p-fluorobenzenesulfonyl)-α-dimethyl glyoxime, bis-O-(p-tert-butylbenzenesulfonyl)-α-dimethyl glyoxime, bis-O-(xylenesulfonyl)-α-dimethyl glyoxime and bis-O-(camphotsulfonyl)-α-dimethyl glyoxime.

Examples of the bissulfone derivative include bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane and bisbenzenesulfonylmethane.

Examples of the β-ketosulfone derivative include 2-cyclohexylcarbonyl-2-(p-toluenesulfonyl)propane and 2-isopropylcarbonyl-2-(p-toluenesulfonyl)propane.

Examples of the disulfone derivative include diphenyldisulfone and dicyclohexyldisulfone.

Examples of the nitrobenzylsulfonate derivative include 2,6-dinitrobenzyl p-toluenesulfonate and 2,4-dinitrobenzyl p-toluenesulfonate.

Examples of the sulfonate derivative include 1,2,3-tris(methanesulfonyloxy)benzene, 1,2,3-tris(trifluoromethanesulfonyloxy)benzene and 1,2,3-tris(p-toluenesulfonyloxy)benzene.

Examples of the sulfonate derivative include N-hydroxyimide compounds such as N-hydroxysuccinimide methanesulfonate, N-hydroxysuccinimide trifluoromethanesulfonate, N-hydroxysuccinimide ethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide 1-octanesulfonate, N-hydroxysuccinimide p-toluenesulfonate, N-hydroxysuccinimide p-methoxybenzenesulfonate, N-hydroxysuccinimide 2-chloroethanesulfonate, N-hydroxysuccinimide benzenesulfotate, N-hydroxysuccinimide 2,4,6-trimethylbenzenesulfonate, N-hydroxysuccinimide 1-naphthalenesulfonate, N-hydroxysuccinimide 2-naphthalenesulfonate, N-hydroxy-2-phenylsuccinimide methanesulfonate, N-hydroxymaleimide methanesulfonate, N-hydroxymaleimide ethanesulfonate, N-hydroxy-2-phenylmaleimide methanesulfonate, N-hydroxyglutarimide methansulfonate, N-hydroxyglutarimide benzensulfonate, N-hydroxyphthalimide methansulfonate, N-hydroxyphthalimide benzensulfonate, N-hydroxyphthalimide trifluoromethanesulfonate, N-hydroxyphthalimide p-toluenesulfonate, N-hydroxynaphthalimide methanesulfonate, N-hydroxynaphthalimide benzenesulfonate, N-hydroxy-5-norbornene-2,3-dicarboxyimide methanesulfonate, N-hydroxy-5-norbornene-2,3-dicarboxyimide trifluoromethanesulfonate and N-hydroxy-5-norbornene-2,3-dicarboxyimide p-toluenesulfonate.

Preferably used are onium salts such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl) sulfonium p-toluenesulfonate, trinaphthylsulfonium trifluoromethanesulfonate, cyclohexylmethyl(2-oxocyclohexyl)sulfonium trifluoromethanesulfonate, (2-norbonyl)methyl(2-oxocyclohexyl)sulfonium trifluoromethanesulfoante and 1,2'-naphthylcarbonylmethyltetrahydrothiophenyum triflate, a diazomethane derivative such as bis(benzenesulfonyl)diazomethane, bis(p-toluenesulfonyl)diazomethane, bis(cyclohexylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane and bis(tert-butylsulfonyl)diazomethane, a glyoxime derivative such as bis-O-(p-toluenesulfonyl)-α-dimethyl glyoxime and bis-O-(n-butanesulfonyl)-α-dimethyl glyoxime, a bissulfone derivative such as bisnaphthylsulfonylmethane, and a sulfonate derivative of N-hydroxyimide compounds such as N-hydroxysuccinimide methanesulfonate, N-hydroxysuccinimide trifluoromethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide p-toluenesulfonate, N-hydroxynaphthalimide methanesulfonate and N-hydroxynaphthalimide benzenesulfonate. The above-described acid generator can be used singly or in combination of two or more. Onium salts are excellent in an effect of improving rectangularity and diazomethane derivatives and glyoxime derivatives are excellent in an effect of decreasing standing wave. Therefore, it is possible to finely control profile by a combination of them.

The amount of the acid generators is preferably from 0.1 to 15 parts by weight, more preferably from 0.5 to 8 parts by weight as a total amount with the photo acid generator of the formula (1) based on 100 parts by weight of a base resin. When the amount is less than 0.1 part by weight, sensitivity may be low, and when it is more than 15 parts by weight, transparency may decrease and the resolution ability of a resist material may decrease.

As the organic solvent used in the present invention, any organic solvent capable of dissolving a base resin, an acid generator, other additives and the like may be used. The organic solvent includes, but not limited to, ketones such as cyclohexanone and methyl-2-n-amylketone, alcohols such as 3-methoxybutanol, 3-methyl-3-methoxybutanol, 1-methoxy-2-propanol and 1-ethoxy-2-propanol, ethers such as propylene glycol monomethyl ether, ethylene glycol monomethyl ether, propylene glycol monoethyl ether, ethylene glycol monoethyl ether, propylene glycol dimethyl ether and diethylene glycol dimethyl ether, and esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate and propylene glycol mono-tert-butyl ether acetate. The solvent can be used singly or in combination of two or more.

In the present invention, preferably used are diethylene glycol dimethyl ether and 1-ethoxy-2-propanol showing most excellent solubility for acid generators in resist components, and among these organic solvents, a propylene glycol monomethyl ether acetate which is a safe solvent, and an admixture thereof.

It is preferable that the amount of the organic solvent is from 200 to 1000 parts by weight, particularly from 400 to 800 parts by weight based on 100 parts by weight of a base resin.

To the resist material of the invention, a dissolution controller can be further added. As the dissolution controller, a compound is added which has an average molecular weight of 100 to 1000, preferably of 150 to 800 and which is obtained by substituting two or more phenolic hydroxyl groups in the molecule by an acid-labile group in an average ratio of 0 to 100 mol % as a whole, or substituting a hydrogen atom on a phenolic hydroxyl group of a compound having a carboxyl group in the molecule by an acid-labile group in an average ratio of 80 to 100 mol % as a whole.

The substitution ratio of the hydrogen atom on the phenolic hydroxyl group or carboxyl group by an acid-labile group is 0 mol % or more, preferably 30 mol % or more on average based on the total amount of the phenolic hydroxyl group or carboxyl group, and its upper limit is 100 mol %, more preferably 80 mol %.

In this case, as the compound having two or more phenolic hydroxyl groups or as the compound having the carboxyl group, those of the following formula (D1) to (D14) are preferable.

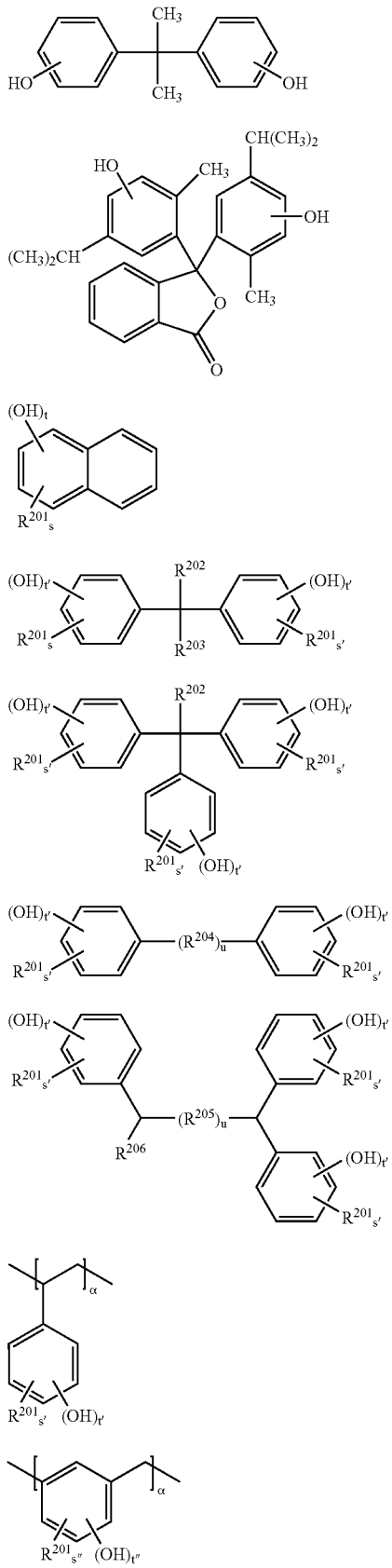

wherein $R^{201}$ and $R^{202}$ each represents a hydrogen atom, or a linear or branched alkyl group or an alkenyl group having 1 to 8 carbon atoms; $R^{203}$ represents a hydrogen atom, or a linear or branched alkyl group or an alkenyl group having 1 to 8 carbon atoms, or —$(R^{207})_h$COOH; $R^{204}$ represents —$(CH_2)_i$— (i=2 to 10), an arylene group having 6 to 10 carbon atoms, a carbonyl group, sulfonyl group, oxygen atom or sulfur atom; $R^{205}$ represents an alkylene group having 1 to 10 carbon atoms, an arylene group having 6 to 10 carbon atoms, a carbonyl group, sulfonyl group, oxygen atom or sulfur atom; $R^{206}$ represents a hydrogen atom, or a linear or branched alkyl group or alkenyl group having 1 to 8 carbon atoms, or a phenyl group or naphthyl group each substituted by a hydroxyl group; $R^{207}$ represents a linear or branched alkylene group having 1 to 10 carbon atoms; $R^{208}$ represents a hydrogen atom or hydroxyl group; the j is an integer of 0 to 5; the u and h each is 0 or 1; the s, t, s', t', s", t" are numbers satisfying s+t=8, s'+t'=5 and s"+t"=4, and having at least one hydroxyl group in each phenyl skeleton; α is a number causing a molecular weight of compounds of the formulae (D8) and (D9) to be 100 to 1000.

In the above formulae, $R^{201}$ and $R^{202}$ each includes a hydrogen atom, methyl group, ethyl group, butyl group, propyl group, ethynyl group and cyclohexyl group. $R^{203}$ includes the same groups as for $R^{201}$ and $R^{202}$, and —COOH and —CH$_2$COOH. $R^{204}$ includes an ethylene group, phenylene group, carbonyl group, sulfonyl group, oxygen atom and sulfur atom. $R^{205}$ includes a methylene group or the same groups as for $R^{204}$. $R^{206}$ includes a hydrogen atom, methyl group, ethyl group, butyl group, propyl group, ethynyl group, cyclohexyl group, and phenyl group or naphthyl group substituted with a hydroxyl group.

Here, the acid-labile group for the dissolution controller includes the same acid-labile groups as those for a base rsin and may be the same as or different from the base resin. Further, it is also possible to add two or more different dissolution inhibitors.

The amount of the dissolution controller is from 0 to 50 parts by weight, preferably from 5 to 50 parts by weight, more preferably from 10 to 30 parts by weight, based on 100 parts by weight of a base resin, and the dissolution controllers can be used singly or in an admixture of two or more. When the amount is less than 5 parts by weight, improvement in resolution may not be obtained, and when it is more that 50 parts by weight, pattern film may decrease and resolution may lower.

The dissolution controller may be synthesized by introducing an acid-labile group to a compound having a phenolic hydroxyl group or carboxyl group, using an organic chemical treatment.

Further, into the resist material of the invention, a basic compound can be added.

As the basic compound, suitable are compounds capable of controlling diffusion speed when acids generated from an acid generator are diffused into a resist film. The addition of a basic compound can control the diffusion speed of an acid in a resist film so that resolution is improved, change in sensitivity after exposure is controlled, dependency on a substrate or environment is lowered, and the degree of exposure allowance and pattern profile and the like is improved.

Such basic compound includes primary, secondary and tertiary aliphatic amines, mixed amines, aromatic amines, heterocyclic amines, nitrogen-containing compounds having a carboxyl group, nitrogen-containing compounds having a sulfonyl group, nitrogen-containing compounds having a hydroxyl group, nitrogen-containing compounds having a hydroxyphenyl group, alcoholic nitrogen-containing compounds, amide derivatives and imide derivatives.

The primary aliphatic amine includes ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine and tetraethylenepentamine.

The secondary aliphatic amine includes dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine and N,N-dimethyltetraethylenepantemine.

Thee tertiary aliphatic amine includes trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine and N,N,N',N'-tetramethyltetraethylenepentamine.

The mixed amine includes dimethylethylamine, methylethylpropyamine, benzylamine, phenetylamine and benzyldimethyamine. Specific examples of the aromatic amines and heterocyclic amines include an aniline derivative such as aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline and N,N-dimethyltoluidine; diephenyl(p-tolyl)amine; methyldiphenylamine; triphenylamine; phenylenediamine; naphthylamine; diaminonaphthalene, pyrrole derivative such as pyrrole, 2H-pyrrole, 1-methylpyrrole, 2,4-dimethylpyrrole, 2,5-dimethylpyrrole and N-methylpyrrole; an oxazole derivative such as oxazole and isooxazole; a thiazole derivative such as thiazole and isothiazole; an imidazole derivative such as imidazole, 4-methylimidazole and 4-methyl-2-phenylimidazole; a pyrazole derivative; a furazane derivative; pyrroline derivative such as pyrroline and 2-methyl-1-pyrroline; a pyrrolidine derivative such as pyrrolidine, N-methylpyrrolidine, pyrrolidinone and N-methylpyrrolidone; an imidazoline derivative; an imidazolidine derivative; a pyridine derivative such as pyridine, methylpyridine, ethylpyridine, propylpyridine, butylpyridine, 4-(1-butylpentyl)pyridine, dimethylpyridine, trimethylpyridine, triethylpyricine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine and dimethylaminopyridine; a pyridazine derivative; a pyrimidine derivative; a pyrazine derivative; a pyrazoline derivative; a pyrazolidine derivative; a piperidine derivative; a piperazine derivative; a morpholine derivative; an indole derivative; an isoindole derivative; a 1H-indazole derivative; an indoline derivative; a quinoline derivative such as quinoline and 3-quinolinecarbonitrile; an isoquinoline derivative; a cinnoline derivative; a quinazoline derivative; a quinoxaline derivative; a phthalazine derivative; a purine derivative; a pteridine derivative; a carbazole derivative; a phenanthridine derivative; an acridine derivative; a phenazine derivative; a 1,10-phenanthroline derivative; an adenine derivative; an adenosine derivative; a guanine derivative; a guianosine derivative; an uracil derivative; and an uridine derivative.

Further, the nitrogen-containing compound having a carboxyl group includes aminobenzoic acid; indolecarboxylic acid; an amino acid derivative such as nicotinic acid, alanine, arginine, aspartic acid, glutamic acid, glycine, histidine, isoleucine, glycylleucine, leucine, methionine, phenylalanine, threonine, lysine, 3-aminopyrazine-2-carboxylic acid and methoxyalanine.

The nitrogen-containing compound having a sulfonyl group includes 3-pyridinesulfonic acid and pyridinium p-toluenesulfonate.

The nitrogen-containing compound having a hydroxyl group, the nitrogen-containing compound having a hydroxylphenyl group and the alcoholic nitrogen-containing compound include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2- hydroxythoxy)ethyl]piperazine, piperidine ethanol, 1-(2-hydroxyethyl)pyrrolidine, 1-(2-hydroxyethyl)-2-pyrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide and N-(2-hydroxyethyl)isonicotineamide. The amide derivative includes formamide, N-methylformamide, N,N-dimethylformamide, acetamide, N-methylacetamide, N,N-dimethylacetamide, propionamide and benzamide. The imide derivative includes phthalimide, succinimide and maleimide.

Further, it is also possible to add one or more compounds selected from basic compounds of the following general formula (B)-1.

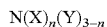  (B)-1

In the formula, n is 1, 2 or 3. The side chain X may be the same or different, and represented by the following general formulae (X)-1 to (X)-3. The side chain Ys may be same or different and each represents a hydrogen atom or a linear, branched or cyclic alkyl group having 1 to 20 carbon atoms, and may contain an ether group or hydroxyl group. Further, Xs may be bonded to form a ring.

Herein, $R^{300}$, $R^{302}$ and $R^{305}$ each represents a linear or branched alkylene group having 1 to 4 carbon atoms. $R^{301}$ and $R^{304}$ each represents a hydrogen atom or a linear, branched or cyclic alkyl group having 1 to 20 carbon atoms, and may contain one or more hydroxyl groups, ether groups, ester groups or lactone rings. $R^{303}$ is a single bond or linear or branched alkylene group having 1 to 4 carbon atoms. $R^{306}$ is a linear, branched or cyclic alkyl group having 1 to 20 carbon atoms, and may contain one or more hydroxyl groups, ether groups, ester groups or lactone rings.

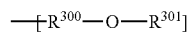  (X)-1

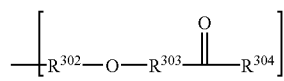  (X)-2

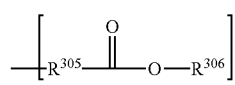  (X)-3

Specific examples of compounds of the general formula (B)-1 include, but are not limited to:

Tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.8.5]eicosane, 1,4,10,13-tetraoxa-7,16-diazabicyclooctadecane, 1-aza-12-crown-4,1-aza-15-crown-5, 1-aza-18-crown-6, tris(2-formyloxyethyl)amine, tris(2-acetoxyethyl)amine, tris(2-propionyloxyethyl)amine, tris(2-butylyloxyethyl)amine, tris(2-isobutylyloxyethyl)amine, tris(2-valeryloxyethyl)amine, tris(2-pivaloyloxyethyl)amine, N,N-bis(2-acetoxyethyl)2-(acetoxyacetoxy)ethylamine, tris(2-methoxycarbonyloxyethyl)amine, tris(2-tert-butoxycarbonyloxyethyl)amine, tris [2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, N,N-bis(2-hydroxyethyl)2-(methoxycarbonyl)ethylamine, N,N-bis(2-acetoxyethyl)2-(methoxycarbonyl)ethylamine, N,N-bis(2-hydroxyethyl)2-(ethoxycarbonyl)ethylamine, N,N-bis(2-acetoxyethyl)2-(ethoxycarbonyl)ethylamine, N,N-bis(2-hydroxyethyl)2-(2-methoxyethoxycarbonyl)ethylamine, N,N-bis(2-acetoxyethyl)2-(2-methoxyethoxycarbonyl)ethylamine, N,N-bis(2-hydroxyethyl)2-(2-hydroxyethoxycarbonyl)ethylamine, N,N-bis(2-acetoxyethyl)2-(2-acetoxyethoxycarbonyl)ethylamine, N,N-bis(2-hydroxyethyl)2-[(methoxycarbonyl)methoxycarbonyl]ethylamine, N,N-bis(2-acetoxyethyl)2-[(methoxycarbonyl)methoxycarbonyl]ethylamine, N,N-bis(2-hydroxyethyl)2-(2-oxopropoxycarbonyl)ethylamine, N,N-bis(2-acetoxyethyl)2-(2-oxopropoxycarbonyl)ethylamine, N,N-bis(2-hydroxyethyl)2-(tetrahydrofurfuryloxycarbonyl)ethylamine, N,N-bis(2-acetoxyethyl)2-(tetrahydrofurfuryloxycarbonyl)ethylamine, N,N-bis(2-hydroxyethyl)2-[(2-oxotetrahydrofuran-3-yl)oxycarbonyl]ethylamine, N,N-bis(2-acetoxyethyl)2-[(2-oxotetrahydrofuran-3-yl)oxycarbonyl]ethylamine, N,N-bis(2-hydroxyethyl)2-(4-hydroxybutoxycarbonyl)ethylamine, N,N-bis(2-formyloxyethyl)2-(4-formyloxybutoxycarbonyl)ethylamine, N,N-bis(2-formyloxyethyl)2-(2-formyloxyethoxycarbonyl)ethylamine, N,N-bis(2-methoxyethyl)2-(methoxycarbonyl)ethylamine, N-(2-hydroxyethyl)bis[2-(methoxycarbonyl)ethyl]amine, N-(2-acetoxyethyl)bis[2-(methoxycarbonyl)ethyl]amine, N-(2-hydroxyethyl)bis[2-(ethoxycarbonyl)ethyl]amine, N-(2-acetoxyethyl)bis[2-(ethoxycarbonyl)ethyl]amine, N-(3-hydroxy-1-propyl)bis[2-(methoxycarbonyl)ethyl]amine, N-(3-acetoxy-1-propyl)bis[2-(methoxycarbonyl)ethyl]amine, N-(2-methoxyethyl)bis[2-(methoxycarbonyl)ethyl]amine, N-butylbis[2-(methoxycarbonyl)ethyl]amine, N-butylbis[2-(2-methoxyethoxycarbonyl)ethyl]amine, N-methylbis(2-acetoxyethyl)amine, N-ethylbis(2-acetoxyethyl)amine, N-methylbis(2-pivaloyloxyethyl)amine, N-ethylbis[2-(methoxycarbonyloxy)ethyl]amine, N-ethylbis[2-(tert-butoxycarbonyloxy)ethyl]amine, tris(methoxycarbonylmethyl)amine, tris(ethoxycarbonylmethyl)amine, N-butylbis (methoxycarbonylmethyl)amine, N-hexylbis (methoxycarbonylmethyl)amine, β-(diethylamino)-δ-valerolactone.

Further, one or more basic compounds having a cyclic structure of the following general formula (B)-2 can also be added.

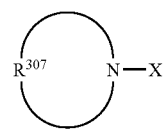  (B)-2 wherein X is as described above; and $R^{307}$ represents a linear or branched alkylene group having 2 to 20 carbon atoms, and may contain one or more carbonyl groups, ether groups, ester groups or sulfides.

Specific examples of (B)-2 include 1-[2-(methoxymethoxy)ethyl]pyrrolidine, 1-[2-(methoxymethoxy)ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino)propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl)propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate and 2-methoxyethyl morpholinoacetate.

Further, basic compounds containing a cyano group of the general formulae (B)-3 to (B)-6 can be added.

 (B)-3

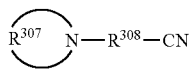 (B)-4

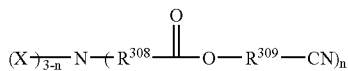 (B)-5

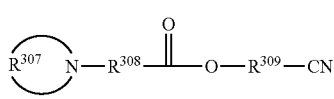 (B)-6 wherein X, $R^{307}$ and n are as described above; and $R^{308}$ and $R^{309}$ may be same or different and each represents the same or different linear or branched alkylene group having 1 to 4 carbon atoms.

Specific examples of the base containing a cyano group include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiononitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]aminoacetonitrile, N-(cyanomethyl)-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-aminopropionate, cyanomethyl 1-pyrrolidinepropionate, cyanomethyl 1-piperidinepropionate, cyanomethyl 4-morpholinepropironate, 2-cyanoethyl 1-pyrrolidinepropionate, 2-cyanoethyl 1-piperidinepropionate and 2-cyanoethyl 4-morpholinepropionate.

The amount of the above basic compound is 0.001 to 10 parts by weight, preferably 0.01 to 1 part by weight based on 1 part by weight of acid generator. When the amount is less than 0.001 parts by weight, an effect as an additive may not be obtained sufficiently and when it is more than 10 parts by weight, resolution and sensitivity may decrease.

Further, in the resist material of the invention, a compound having a group ≡C—COOH in the molecule can be comprised.

The compound having a group ≡C—COOH in the molecule includes, but not limited to, one or more compounds selected from the group I and group II described below. The addition of this compound may improve PED stability of a resist and edge roughness on a nitride film substrate.

[Group I]

Compounds obtained by substituting a part or all of the hydrogen atom of a phenolic hydroxyl groups on the compound selected from the following general formulae (A1) to (A10) by —$R^{401}$—COOH wherein $R^{401}$ represents a linear or branched alkylene group having 1 to 10 carbon atoms, and a molar ratio in the molecule of a phenolic hydroxyl group (C) to the group (C) plus a group ≡C—COOH: C/(C+D), is 0.1 to 1.0.

[Group II]

Compounds of the following general formulae (A11) to (A15).

A1
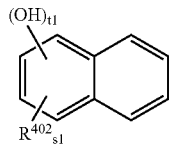

A2
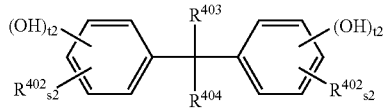

A3
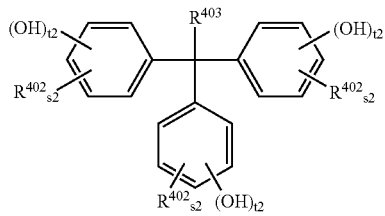

A4
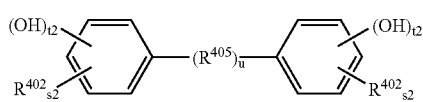

A5
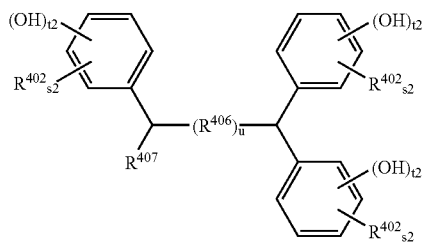

A6
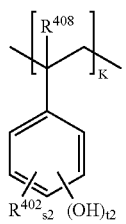

A7
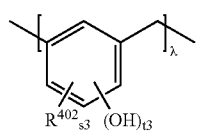

A8
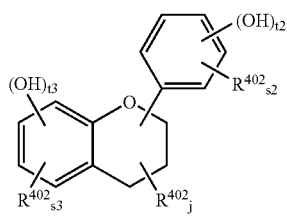

-continued

A9
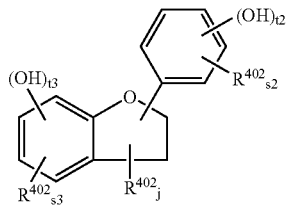

A10
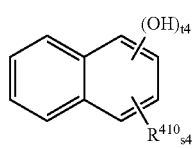

A11
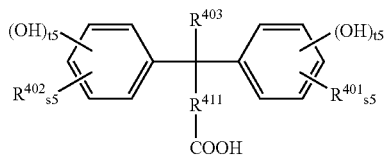

A12
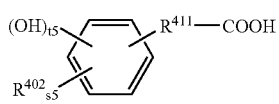

A13
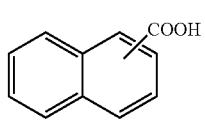

A14
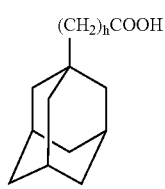

A15
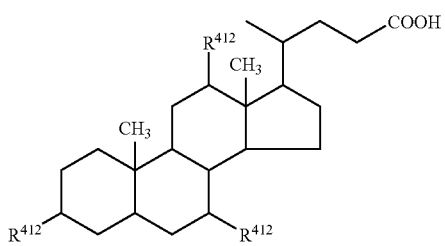

In the formula, $R^{408}$ represents a hydrogen atom or methyl group. $R^{402}$ and $R^{403}$ each represents a hydrogen atom, or a linear or branched alkyl group or alkenyl group having 1 to 8 carbon atoms. $R^{404}$ represents a hydrogen atom, or a linear or branched alkyl group or alkenyl group having 1 to 8 carbon atoms, or —$(R^{409})_h$COOR' group wherein R' represents a hydrogen atom or —$R^{409}$—COOH. $R^{405}$ represents —$(CH_2)_i$— (i=2 to 10), an arylene group having 6 to 10 carbon atoms, a carbonyl group, sulfonyl group, oxygen atom or sulfur atom. $R^{406}$ represents an alkylene group having 1 to 10 carbon atoms, an arylene group having 6 to 10 carbon atoms, a carbonyl group, sulfonyl group, oxygen atom or sulfur atom. $R^{407}$ represents a hydrogen atom, or a linear or branched alkyl group or alkenyl group having 1 to 8 carbon atoms, or a phenyl group or naphthyl group each substituted by a hydroxyl group. $R^{409}$ represents a linear or branched alkylene group having 1 to 10 carbon atoms. $R^{410}$ represents a linear or branched alkyl group or an alkylene group having 1 to 8 carbon atoms or —$R^{411}$—COOH group. $R^{411}$ represents a linear or branched alkylene group having 1 to 10 carbon atoms. The j represents an integer of 0 to 5. The u and h each is 0 or 1. The s1, t1, s2, t2, s3, t3, s4 and t4 each is a number satisfying s1+t1=8, s2+t2=5, s3+t3=4 and s4+t4=6, and giving at least one hydroxyl group in each phenyl skeleton. The κ is a number such that a weight-average molecular weight of the compound of formula (A6) is 1,000 to 5,000. The λ is a number such that a weight-average molecular weight of the compound of formula (A7) is 1,000 to 10,000. $R^{412}$ represents a hydrogen atom or hydroxyl group. S5 and t5 each is a number satisfying s5≧0, t5≧0 and s5+t5=5. The h' is 0 or 1.

Specific examples of the compound in the invention include, but not limited to, compounds of the following general formulae AI-1 to 14 and AII-1 to 10.

AI-1
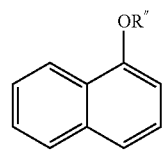

AI-2
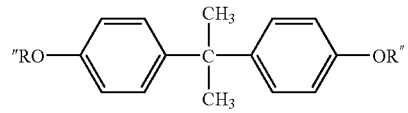

AI-3
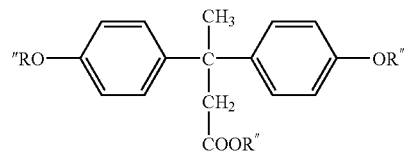

AI-4
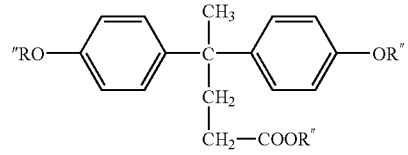

AI-5
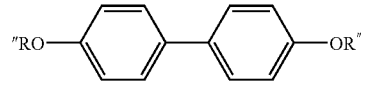

AI-6
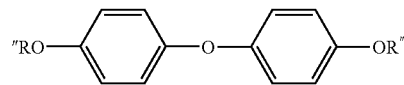

AI-7
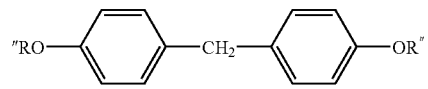

AI-8
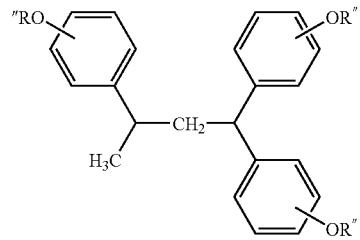

AI-9
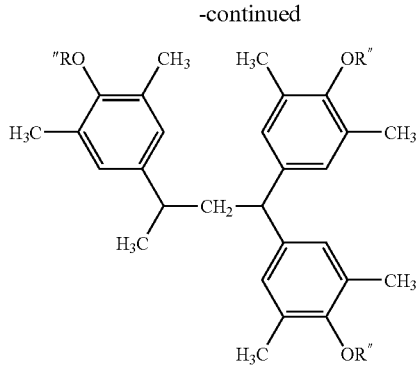

AI-10
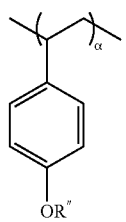

AI-11
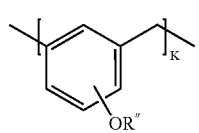

AI-12
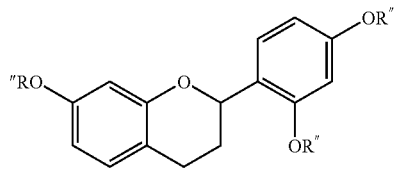

AI-13
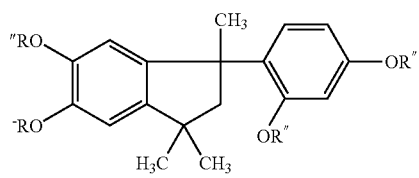

AI-14
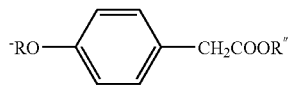

In the above formulae R" represents a hydrogen atom or CH$_2$COOH group, and 10 to 100 mol % of R" in each compound is a CH$_2$COOH group. The α and κ are as defined above.

AII-1
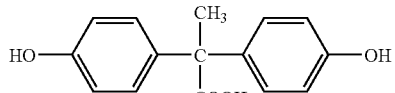

AII-2
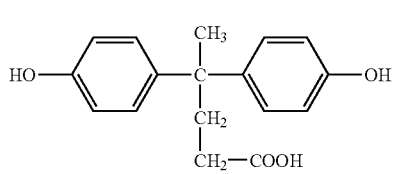

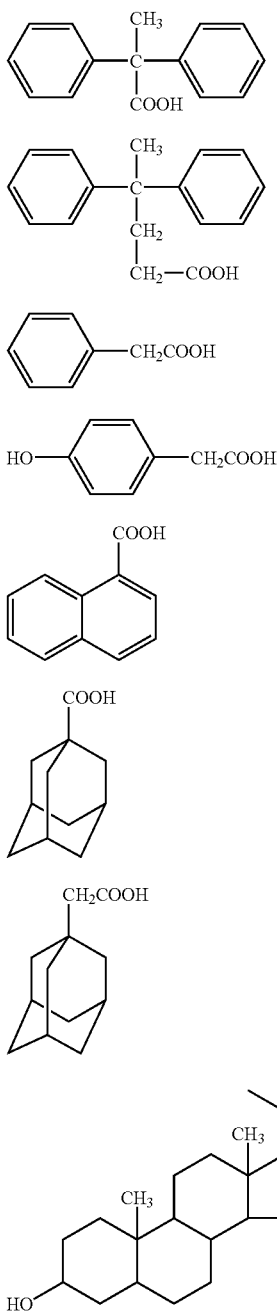

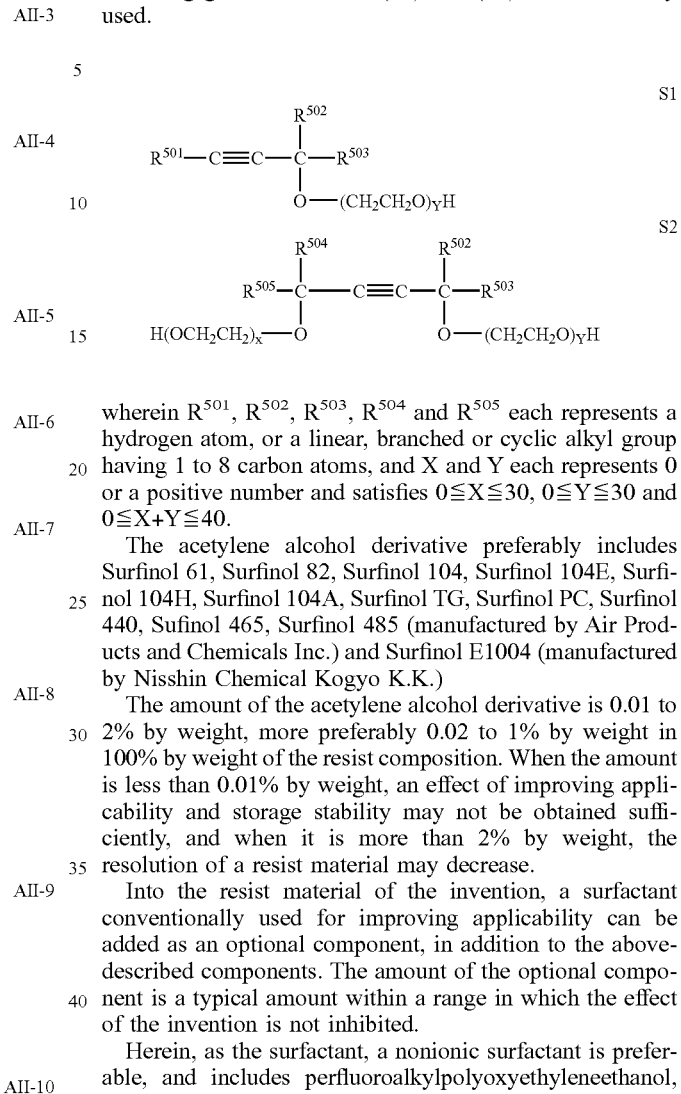

The compound having a group of ≡C—COOH in the molecule can be used singly or in combination of two or more.

The amount of the compound having the group ≡C—COOH in a molecule is 0 to 5 parts by weight, preferably 0.1 to 5 parts by weight, more preferably 0.1 to 3 parts by weight, further preferably 0.1 to 2 parts by weight based on 100 parts by weight of a base resin. When the amount is more than 5 parts by weight, the resolution of a resist material may decrease.

Further, into the resist material of the invention, an acetylene alcohol derivative can be comprised as an additive, and thereby storage stability can be improved.

As the acetylene alcohol derivative, compounds of the following general formulae (S1) and (S2) can be suitably used.

wherein $R^{501}$, $R^{502}$, $R^{503}$, $R^{504}$ and $R^{505}$ each represents a hydrogen atom, or a linear, branched or cyclic alkyl group having 1 to 8 carbon atoms, and X and Y each represents 0 or a positive number and satisfies $0 \leq X \leq 30$, $0 \leq Y \leq 30$ and $0 \leq X+Y \leq 40$.

The acetylene alcohol derivative preferably includes Surfinol 61, Surfinol 82, Surfinol 104, Surfinol 104E, Surfinol 104H, Surfinol 104A, Surfinol TG, Surfinol PC, Surfinol 440, Sufinol 465, Surfinol 485 (manufactured by Air Products and Chemicals Inc.) and Surfinol E1004 (manufactured by Nisshin Chemical Kogyo K.K.)

The amount of the acetylene alcohol derivative is 0.01 to 2% by weight, more preferably 0.02 to 1% by weight in 100% by weight of the resist composition. When the amount is less than 0.01% by weight, an effect of improving applicability and storage stability may not be obtained sufficiently, and when it is more than 2% by weight, the resolution of a resist material may decrease.

Into the resist material of the invention, a surfactant conventionally used for improving applicability can be added as an optional component, in addition to the above-described components. The amount of the optional component is a typical amount within a range in which the effect of the invention is not inhibited.

Herein, as the surfactant, a nonionic surfactant is preferable, and includes perfluoroalkylpolyoxyethyleneethanol, fluorinated alkyl esters, perfluoroalkylamine oxide, perfluoroalkyl ethylene oxide (EO) adducts, fluorine-containing organosiloxane compounds. Examples thereof include Florad FC-430, FC-431 (both manufactured by Sumitomo 3M Ltd.), Surflon S-141, S-145 (both manufactured by Asahi Glass Co. Ltd.), Unidaine DS-401, DS-403, DS-451 (all manufactured by Daikin Industries, Ltd.), Megafac F-8151 (manufactured by Dainippon Ink & Chemicals Inc.), X-70-092, X-70-093 (all manufactured by Shin-Etsu Chemical Co. Ltd.). Florad FC-430 (manufactured by Sumitomo 3M Ltd.) and X-70-093 (manufactured by Shin-Etsu Chemical Co. Ltd.) are preferably mentioned.

To form patterns using the resist material of the invention, known lithography technologies can be adopted. For example, the resist material is applied on a substrate such as silicon wafer by means such as spin coating so that the film thickness is 0.3 to 2.0 μm, and pre-baked on a hot plate at 60 to 150° C. for 1 to 10 minutes, preferably at 80 to 130° C. for 1 to 5 minutes. Next, a mask for forming the intended pattern is placed on the resist film, ArF excimer laser is irradiated at an exposure of about 1 to 100 mJ/cm², preferably 5 to 50 mJ/cm². Then, the resist film is subjected to post exposure bake (PEB) on a hot plate at 60 to 150° C. for 1 to 5 minutes, preferably at 80 to 130° C. for 1 to 3 minutes.

This heating is necessary when a dissociation reaction of an acid-labile group does not occur easily and sufficient resolution is not obtained, without heating. Further, using a developer of an aqueous alkali solution such as tetramethylammonium hydroxide (TMAH) of 0.1 to 5% by weight, preferably of 2 to 3% by weight, development is conducted according to an ordinary method such as a dip method, puddle method or spray method for 0.1 to 3 minutes, preferably for 0.5 to 2 minutes, to form the intended pattern on the substrate. When the amount is out of the above-described upper limit or lower limit, the intended pattern may not be obtained.

The present invention is specifically explained based on following examples and comparative examples. However, the it should not be construed that the present invention is limit to them.

SYNTHESIS EXAMPLE 1

Synthesis of the Following Compound (syn-1)

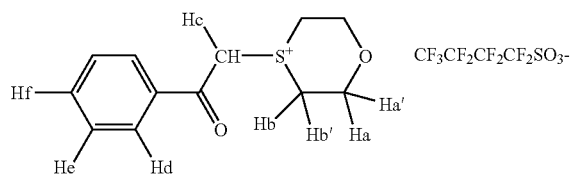

(Syn-1)

Ten grams (0.05 mol) of α-bromoacetophenone was dissolved in 30 g of nitromethane, and to this was added 5.2 g (0.05 mol) of 1,4-thioxane, and the mixture was stirred at room temperature for 24 hours. To the reaction solution were added 100 g of water and 100 g of diethyl ether to cause liquid separation. To the aqueous phase was added 16.9 g (0.05 mol) of potassium nonafluoro-n-butanesulfonate and 200 g of dichloromethane and the resulting aqueous mixture was stirred. The separated organic phase was washed with 200 g of water, and the solvent was removed by a rotary evaporator. To the resulted oily substance was added diethyl ether to cause re-crystallization. The crystal was filtrated under suction, washed with diethyl ether, and then dried under reduced pressure. The data of nuclear magnetic resonance (NMR) spectrum and infrared (IR) spectrum and time-of-flight mass spectrometry (TOFMS) of the intended substance obtained at a yield of 3.4 g (yield: 13%) are shown below.

($^1$HNMR(CD$_3$OD); ppm) 3.35–3.46(2H, m, Ha), 3.63–3.74(2H, m, Ha'), 4.03–4.12(2H, m, Hb), 4.26–4.360 (2H, m, Hb'), 4.84(2H, s, Hc), 7.57–7.63(2H, t, He), 7.73–7.78(1H, t, Hf), 8.08–8.10(2H, d, Hd). (IR; cm$^{-1}$) 2981, 2927, 1678, 1599, 1583, 1454, 1425, 1388, 1354, 1332, 1305, 1254, 1221, 1165, 1134, 1103, 1060, 1051, 1016, 991, 976, 872, 847, 837, 804, 752, 736, 698, 682, 659, 640, 628, 619, 600, 565, 532.

(TOFMS)
Positive electrode (+) M$^+$: 223 (corresponding to PhCOCH$_2$S$^+$=(CH$_2$CH$_2$)$_2$=O)
Negative electrode (−) M$^-$: 299 (corresponding to C$_4$F$_9$SO$_3^-$)

SYNTHESIS EXAMPLE 2

Synthesis of Sodium 4-(4'-methylphenylsulfonyloxy)benzenesulfonate

The intended sodium sulfonate was synthesized by using 4-phenolsulfonic acid hydrate and p-toluenesulfonyl chloride in a solvent mixture of tetrahydroguran and water, while dropping an aqueous sodium hydroxide solution, with reference to the synthesis method described in Japanese Patent Provisional Publication No. 2001-122850 (U.S. Pat. No. 6,440,634).

SYNTHESIS EXAMPLE 3

Synthesis of the Following Compound 3 (syn-3)

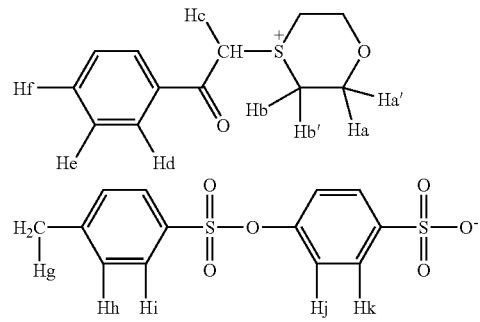

(Syn-3)

The intended substance was synthesized in the same manner as in Synthesis Example 1 except that 17.5 g (0.05 mol) of sodium 4-(4'-methylphenylsulfonyloxy)benzenesulfonate obtained in Synthesis Example 2 was used in the place of potassium nonafluoro-n-butanesulfonate used in Synthesis Example 1. The data of nuclear magnetic resonance (NMR) spectrum and infrared (IR) spectrum and time-of-flight mass spectrometry (TOFMS) of the intended substance obtained at a yield of 2.0 g (yield: 7%) are shown below.

($^1$HNMR(CD$_3$OD); ppm) 2.42(3H, s, Hg), 3.35–3.46(2H, m, Ha), 3.63–3.74(2H, m, Ha'), 4.03–4.12(2H, m, Hb), 4.26–4.36(2H, m, Hb'), 4.84(2H, s, Hc), 6.95–6.97(2H, d, Hj), 7.46–7.48(2H, d, Hh), 7.55–7.57(2H, d, Hi), 7.59–7.64 (2H, t, He), 7.72–7.79(3H, m, Hf, Hk), 8.00–8.02(2H, d, Hd). (IR; cm$^{-1}$) 1678, 1599, 1486, 1454, 1378, 1353, 1332, 1305, 1254, 1221, 1165, 1133, 1103, 1051, 1033, 1016, 1012, 991, 872, 858, 848, 753, 686, 659, 609, 600, 568, 553.

(TOFMS)
Positive electrode (+) M$^+$: 223 (corresponding to PhCOCH$_2$S$^+$=(CH$_2$CH$_2$)$_2$=O)
Negative electrode (−) M$^-$: 327 (corresponding to CH$_3$PhSO$_3$PhSO$_3^{-1}$)

SYNTHESIS EXAMPLE 4

Synthesis of the Following Compound (syn-4)

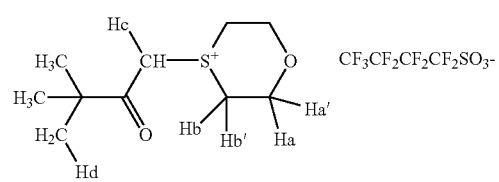

(Syn-4)

Synthesis was conducted in the same manner as in Synthesis Example 1 except that 8.95 g (0.05 mol) of 1-bromo-3,3-dimethyl-2-butanone was used in the place of α-bromoacetophenone in Synthesis Example 1. The data of nuclear magnetic resonance (NMR) spectrum and infrared (IR) spectrum and-time-of-flight mass spectrometry (TOFMS) of the intended substance obtained at a yield of 2.5 g (yield: 10%) are shown below.

($^1$HNMR(CD$_3$OD); ppm) 1.11(9H, s, Hd), 3.35–3.46(2H, m, Ha), 3.63–3.74(2H, m, Ha'), 4.03–4.12(2H, m, Hb), 4.26–4.36(2H, m, Hb'), 4.84(2H, s, Hc), 7.57–7.63(2H, t, He), 7.73–7.78(1H, t, Hf), 8.08–8.10(2H, d, Hd). (IR; cm$^{-1}$) 2976, 1714, 1481, 1371, 1355, 1254, 1220, 1211, 1133, 1101, 1059, 1005, 991, 804, 739, 698, 657, 640, 619, 600, 522.

(TOFMS)

Positive electrode (+) M$^+$: 203 (corresponding to (CH$_3$)$_3$CCOCH$_2$S$^+$=(CH$_2$CH$_2$)$_2$=O)

Negative electrode (−) M$^-$: 299 (corresponding to C$_4$F$_9$SO$_3^-$)

EVALUATION EXAMPLES

Sensitivity and resolution for the resist comprising the photo acid generators (PAG1 to 10) represented by the following formulae were evaluated.

(PAG 1)
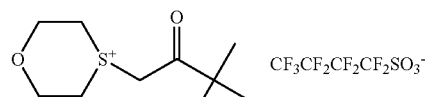

(PAG 2)
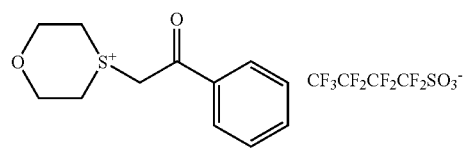

(PAG 3)
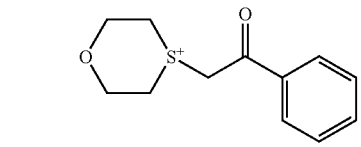

(PAG 4)
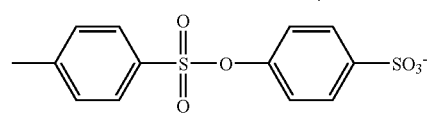

(PAG 5)
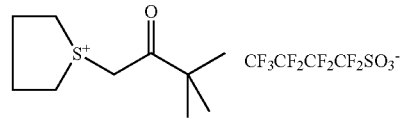

(PAG 6)
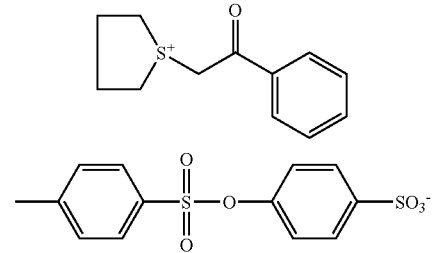

(PAG 7)
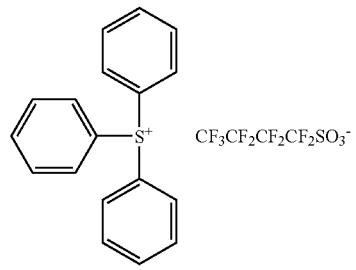

(PAG 8)
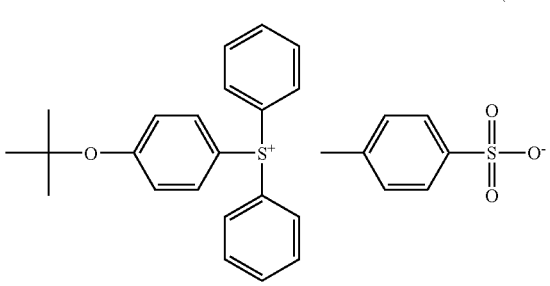

(PAG 9)
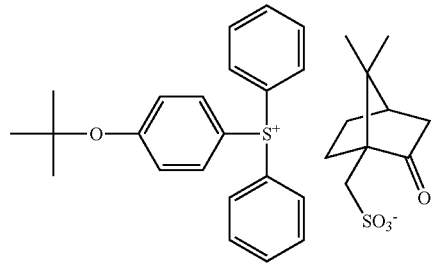

(PAG 10)
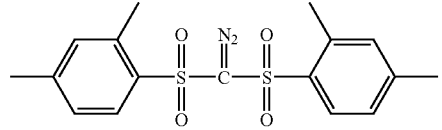

Examples 1 to 40

Evaluation of Resolution of Resist

Photo acid generators (PAG 1 to 10) represented by the above formulae, polymers of the following formulae (Polymer 1 to 28) as a base resin, dissolution inhibitors (DRR 1 to 4) of the following formulae, a basic compound, and compounds having a group ≡C—COOH in the molecule of the following formulae (ACC 1, 2) were dissolved in a solvent containing 0.01 wt % of FC-430 (manufactured by Sumitomo 3M Ltd.) to prepare resist materials. Then, the compositions were filtrated through a 0.2 μm Teflon (trade mark) filter to yield resist solutions.

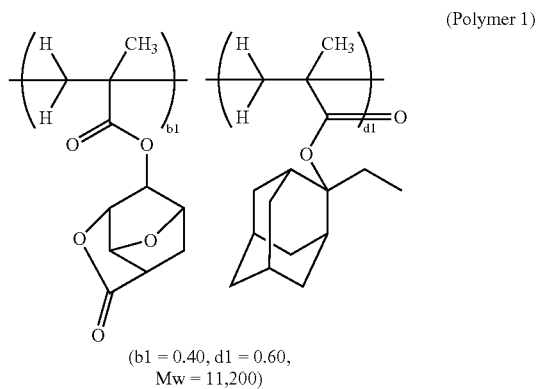

(Polymer 1)
(b1 = 0.40, d1 = 0.60, Mw = 11,200)

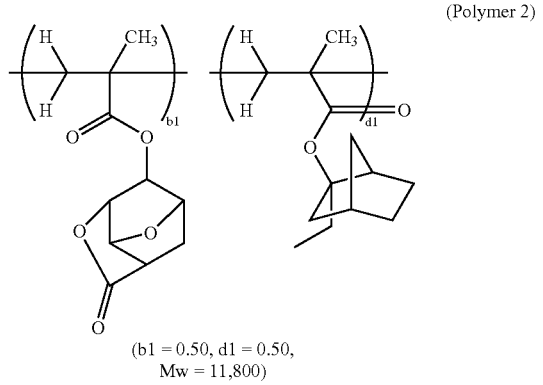

(Polymer 2)
(b1 = 0.50, d1 = 0.50, Mw = 11,800)

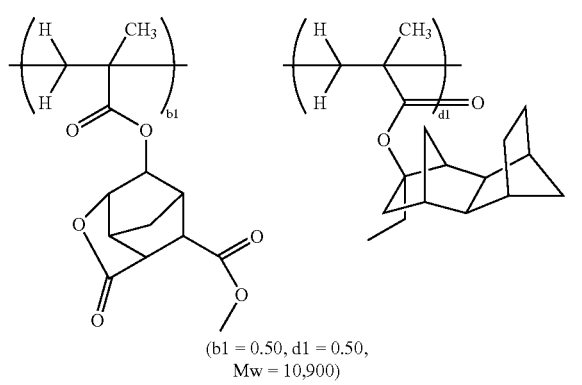

(Polymer 3)
(b1 = 0.50, d1 = 0.50, Mw = 10,900)

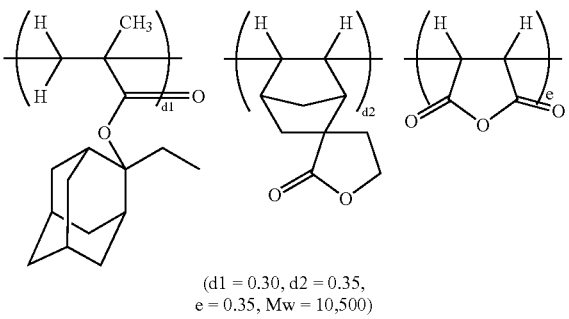

(Polymer 4)
(d1 = 0.30, d2 = 0.35, e = 0.35, Mw = 10,500)

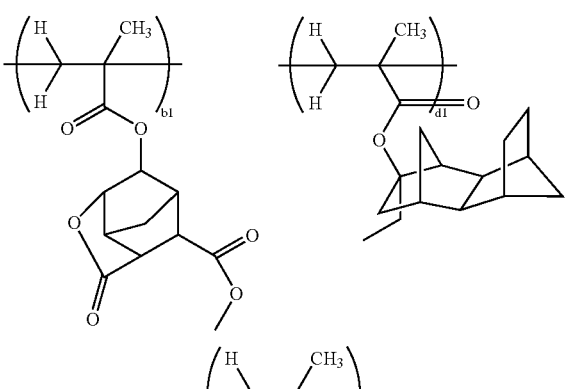

(Polymer 5)
(b1 = 0.40, d1 = 0.30, d2 = 0.30, Mw = 12,500)

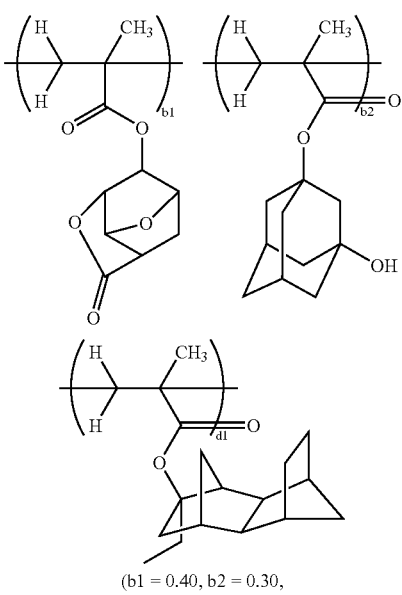

(Polymer 6)
(b1 = 0.40, b2 = 0.30, d1 = 0.30, Mw = 11,200)

(Polymer 7)
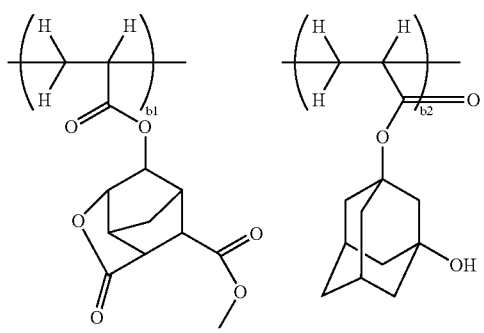
(b1 = 0.40, b2 = 0.20,
d1 = 0.40, Mw = 12,800)
(Polymer 8)
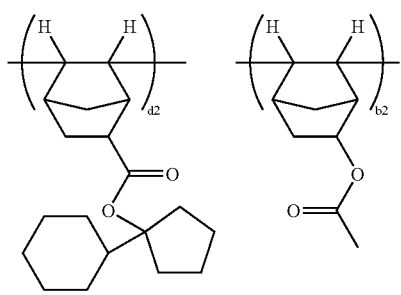
(d2 = 0.35, b2 = 0.15,
e = 0.50, Mw = 8,300)
(Polymer 9)
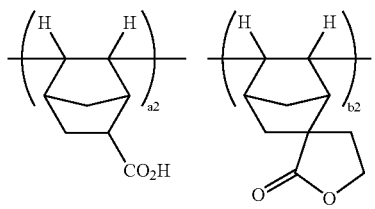
(a2 = 0.10, b2 = 0.30,
d1 = 0.60, Mw = 27,600)
(Polymer 10)
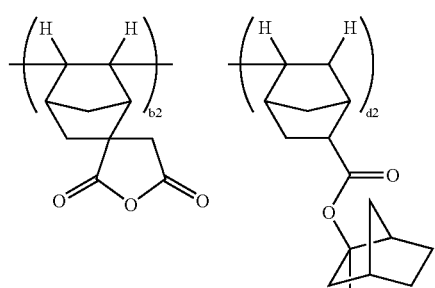
(b2 = 0.40, d2 = .60, Mw = 18,300)
(Polymer 11)
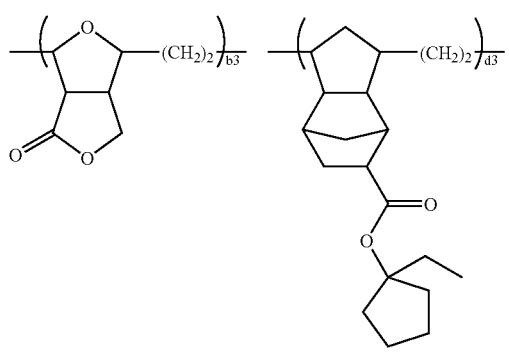
(b3 = 0.50, d3 = .50,
Mw = 29,100)
(Polymer 12)
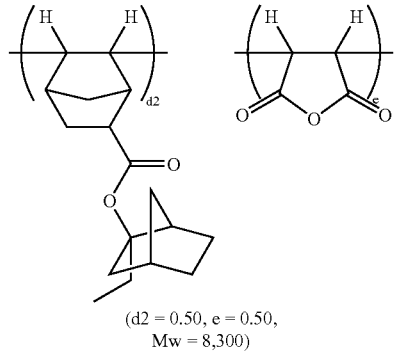
(d2 = 0.50, e = 0.50,
Mw = 8,300)
(Polymer 13)
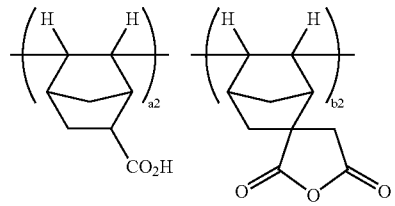
(a2 = 0.10, b2 = 0.30,
d1 = 0.60, Mw = 27,600)

-continued
(Polymer 14)
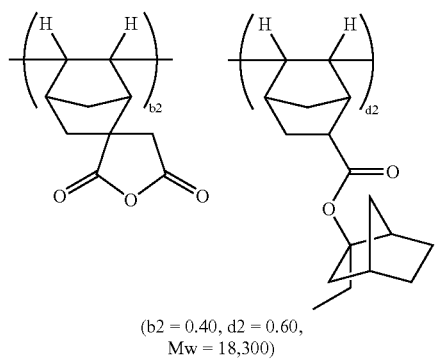
(b2 = 0.40, d2 = 0.60, Mw = 18,300)
(Polymer 15)
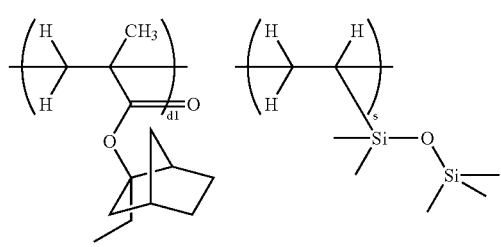
(b3 = 0.40, d3 = 0.60, Mw = 29,100)
(Polymer 16)
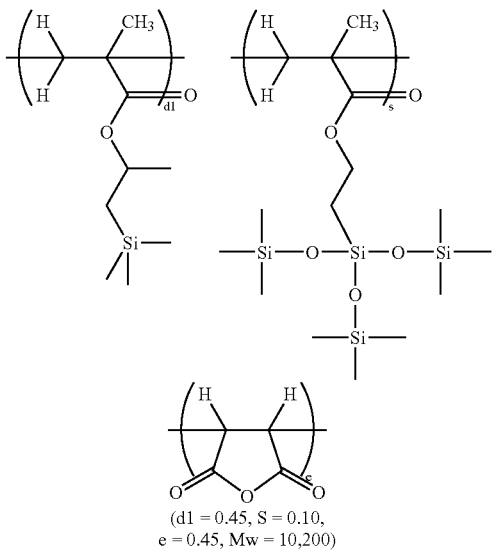
(d1 = 0.40, S = 0.20, e = 0.40, Mw = 10,200)
-continued
(Polymer 17)
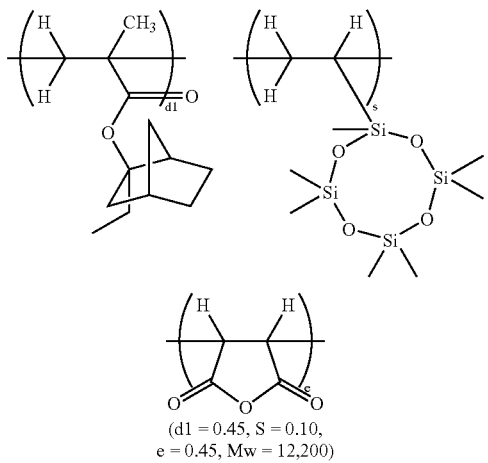
(d1 = 0.45, S = 0.10, e = 0.45, Mw = 12,200)
(Polymer 18)
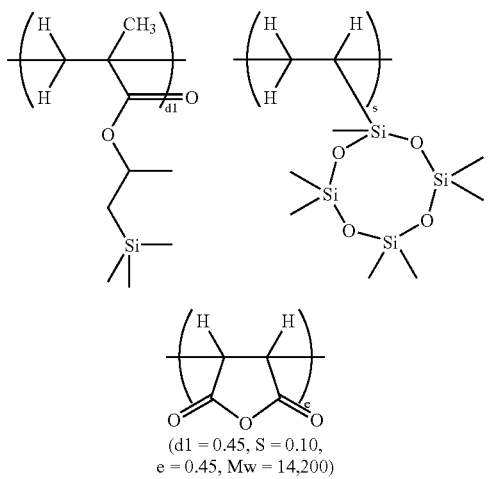
(d1 = 0.45, S = 0.10, e = 0.45, Mw = 14,200)
(Polymer 19)
(d1 = 0.45, S = 0.10, e = 0.45, Mw = 10,200)

-continued
(Polymer 20)
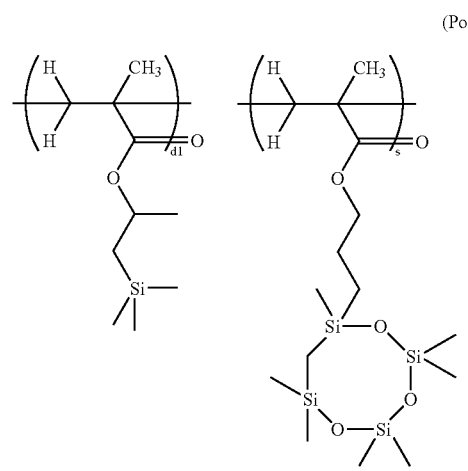
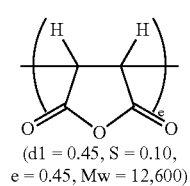
(d1 = 0.45, S = 0.10, e = 0.45, Mw = 12,600)
(Polymer 21)
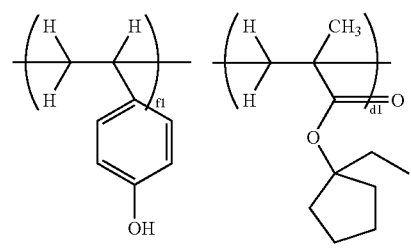
(f1 = 0.70, d1 = 0.30, Mw = 14200)
(Polymer 22)
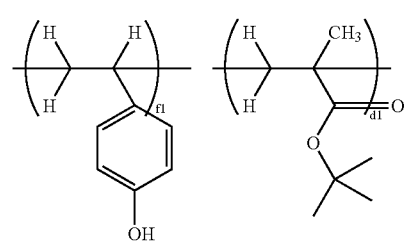
(f1 = 0.65, d1 = 0.35, Mw = 13600)
(Polymer 23)
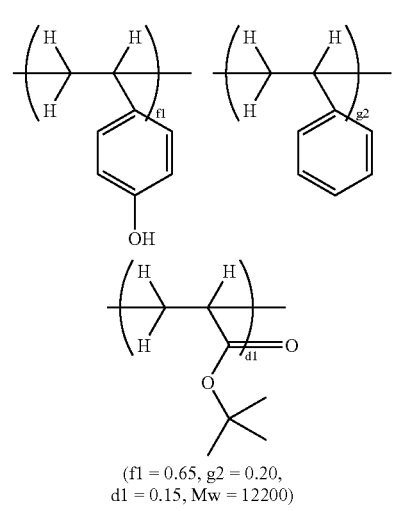
(f1 = 0.65, g2 = 0.20, d1 = 0.15, Mw = 12200)
(Polymer 24)
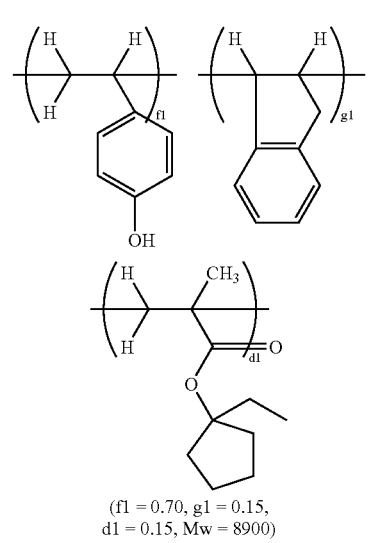
(f1 = 0.70, g1 = 0.15, d1 = 0.15, Mw = 8900)
(Polymer 25)
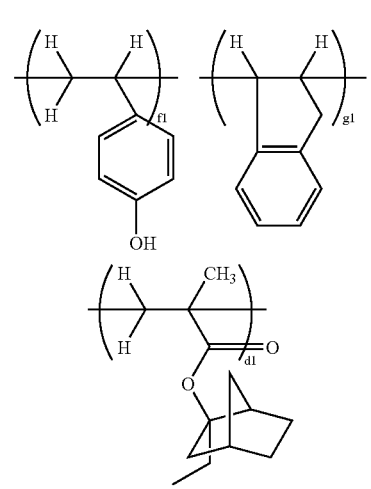
(f1 = 0.70, g1 = 0.13, d1 = 0.12, Mw = 9800)

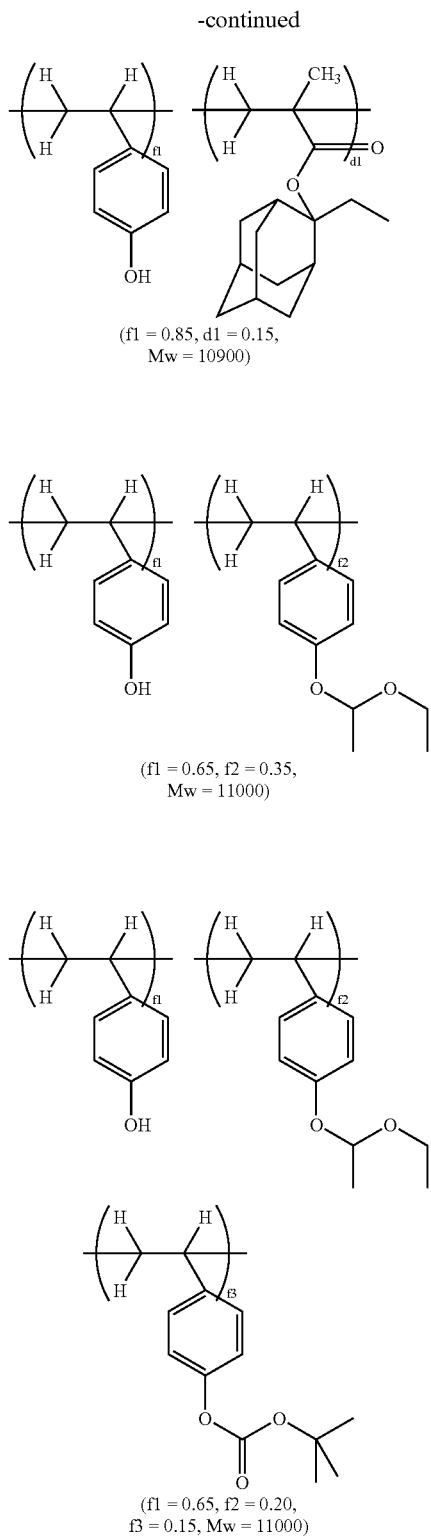

ArF Exposure Example

Resists using Polymers 1 to 20 were exposed to ArF (wavelength: 193 nm)

A reflection prevention film solution (AR19 manufactured by Shipley Co., Ltd.) was applied on a silicon substrate and baked at 200° C. for 60 seconds to produce a reflection preventing film (thickness: 82 nm). Then, a resist solution was spin-coated thereon and then baked at 110° C. for 60 seconds using a hot plate to produce a resist film having a thickness of 300 nm. The resist film was exposed using an ArF excimer laser micro stepper (manufactured by Nikon Corp., NA=0.55, σ0.7), and baked (PEB) at 110° C. for 90 seconds, and developed for 30 seconds using a 2.38 wt % aqueous solution of tetramethylammonium hydroxide.

For evaluation of the resist, the exposure amount resolving 0.20 μm group line and space by 1:1 was defined as an optimal exposure amount (Eop, mJ/cm$^2$). The minimum line width (μm) of line-and space pattern separated at the optimal exposure amount was regarded as the resolution of the evaluation resist. The width of isolated line of line and space 1:10 at the same exposure amount was measured and a value obtained by subtracting the line width of the isolated line from the line width of the group line was used as a dimension difference (I/G bias) between an isolated pattern and a dense pattern. Unevenness of the group line was measured as line-edge roughness. The results are-shown in Tables 1 and 2.

KrF Exposure Example

Resists using Polymers 21 to 28 were exposed to KrF (wavelength: 248 nm)

A reflection prevention film solution (DUV-3 manufactured by Brewer Science Co., Ltd.) was applied on a silicon substrate, baked at 200° C. for 60 seconds to produce a reflection preventing film (film thickness: 55 nm). A resist solution was spin-coated thereon and then baked at 100° C. for 60 seconds using a hot plate to produce a resist film having a thickness of 400 nm. The resist film was exposed using a KrF excimer laser scanner (S203B, manufactured by Nikon Corp., NA=0.68, s=0.75), baked (PEB) at 110° C. for 90 seconds, and developed for 60 seconds using a 2.38 wt % aqueous solution of tetramethylammonium hydroxide.

For evaluation of the resist, the exposure amount resolving 0.18 μm group line and space by 1:1 was defined as an optimal exposure amount (Eop, mJ/cm$^2$). The minimum line width (μm) of line and space pattern separated at the optimal exposure amount was regarded as the resolution of the evaluation resist. The line width of isolated lines of line and space 1:10 at the same exposure amount was measured and a value obtained by subtracting the line width of the isolated line from the line width of the group line was used as a dimension difference (I/G bias) between an isolated pattern and a dense pattern. Unevenness of the group line was measured as line-edge roughness. The results are shown in Tables 2 and 3.

The composition of the resists and the evaluation results therefor are shown in Tables 1 to 3. The abbreviation for the solvents and basic compounds in Tables 1 and 2 compounds are shown below.

PGMEA: propylene glycol methyl ether acetate
CyHO: cyclohexanone
PG/EL: mixed solvent of 70 wt % PGMEA and 30 wt % ethyl lactate
TBA: tributylamine
TEA: triethanolamine
TMMEA: trismethoxymethoxyethylamine
TMEMEA: trismethoxyethoxymethoxyethylamine
AAA: tris(2-acetoxyethyl)amine
AACN: N,N-bis(2-acetoxyethyl)-3-aminopropiononitrile

COMPARATIVE EXAMPLE

For comparison, sensitivity and resolution for the resists were evaluated for sulfonium salts (PAG 4 to 6) of the following formulae.

Comparative Examples1 to 6

Using the sulfonium salts (PAG 4 to 6) of the above formulae, the resists were prepared in the same manner as described above at compositions shown in Table 4, and exposure was conducted using an ArF micro-stepper in the same manner as described above, and sensitivity and resolution were evaluated.

The compositions of the resists and evaluation results therefore are shown in Table 4.

From the results shown in Tables 1 to 4, it has been confirmed that the resist materials of the invention have higher sensitivity and higher resolution as compared with conventional materials, and further excel in line-edge roughness and I/G bias.

TABLE 1

| Example | Resin (part by weight) | Acid generator (part by weight) | Dissolution inhibitor or ograginc acid (part by weight) | Basic compoud (part by weight) | solvent (part by weight) | Optimum exposure (mJ/cm$^2$) | Resolution (μm) | I/G bias (nm) | line-edge roughness (nm) |
|---|---|---|---|---|---|---|---|---|---|
| 1 | Polymer1 (80) | PAG1 (8.0) | — | TBA (0.10) | PGMEA (480) | 44.0 | 0.16 | 25 | 5.0 |
| 2 | Polymer1 (80) | PAG2 (3.0) | — | TBA (0.10) | PGMEA (480) | 30.0 | 0.15 | 21 | 2.8 |
| 3 | Polymer1 (80) | PAG3 (3.0) | — | TBA (0.10) | PGMEA (480) | 36.0 | 0.16 | 32 | 3.2 |
| 4 | Polymer1 (80) | PAG1 (4.0) PAG2 (1.5) | — | TBA (0.10) | PGMEA (480) | 38.0 | 0.16 | 23 | 4.0 |
| 5 | Polymer1 (80) | PAG2 (1.5) PAG3 (1.5) | — | TBA (0.10) | PGMEA (480) | 32.0 | 0.16 | 28 | 3.0 |
| 6 | Polymer1 (80) | PAG2 (1.5) PAG7 (1.0) | — | TBA (0.10) | PGMEA (480) | 28.0 | 0.15 | 18 | 7.8 |
| 7 | Polymer2 (80) | PAG2 (3.0) | — | TBA (0.10) | PGMEA (480) | 21.0 | 0.16 | 22 | 3.9 |
| 8 | Polymer3 (80) | PAG2 (3.0) | — | TBA (0.10) | PGMEA (480) | 18.0 | 0.15 | 22 | 3.5 |
| 9 | Polymer4 (80) | PAG2 (3.0) | — | TBA (0.10) | PGMEA (480) | 25.0 | 0.15 | 15 | 9.1 |

TABLE 1-continued

| Example | Resin (part by weight) | Acid generator (part by weight) | Dissolution inhibitor or ograginc acid (part by weight) | Basic compound (part by weight) | solvent (part by weight) | Optimum exposure (mJ/cm$^2$) | Resolution (μm) | I/G bias (nm) | line-edge roughness (nm) |
|---|---|---|---|---|---|---|---|---|---|
| 10 | Polymer5 (80) | PAG2 (3.0) | — | TBA (0.10) | PGMEA (480) | 34.0 | 0.17 | 31 | 5.0 |
| 11 | Polymer6 (80) | PAG2 (3.0) | — | TBA (0.10) | PGMEA (480) | 22.0 | 0.15 | 19 | 3.0 |
| 12 | Polymer7 (80) | PAG2 (3.0) | — | TBA (0.10) | PGMEA (480) | 32.0 | 0.17 | 41 | 6.1 |
| 13 | polymer8 (80) | PAG2 (3.0) | — | TBA (0.10) | PGMEA (480) | 26.0 | 0.18 | 24 | 7.1 |
| 14 | Polymer9 (80) | PAG1 (3.0) | ACC1 | TBA (0.10) | CyHO (560) | 24.0 | 0.16 | 35 | 4.2 |
| 15 | Polymer10 (80) | PAG1 (3.0) | ACC2 | TBA (0.10) | CyHO (560) | 22.0 | 0.16 | 37 | 3.3 |

TABLE 2

| Example | Resin (part by weight) | acid generator (part by weight) | dissolution inhibitor or ograginc acid (part by weight) | Basic compoud (part by weight) | solvent (part by weight) | Optimum exposure (mJ/cm$^2$) | Resolution (μm) | I/G bias (nm) | line-edge roughness (nm) |
|---|---|---|---|---|---|---|---|---|---|
| 16 | Polymer11 (80) | PAG2 (3.0) | — | TBA (0.10) | CyHO (560) | 22.0 | 0.18 | 42 | 3.2 |
| 17 | Polymer12 (80) | PAG2 (3.0) | — | TBA (0.10) | PGMEA (480) | 21.0 | 0.15 | 27 | 8.7 |
| 18 | Polymer13 (80) | PAG2 (3.0) | DRR1 | TBA (0.10) | CyHO (560) | 29.0 | 0.15 | 42 | 2.3 |
| 19 | Polymer14 (80) | PAG2 (3.0) | DRR2 | TBA (0.10) | CyHO (560) | 18.0 | 0.18 | 41 | 5.2 |
| 20 | Polymer15 (80) | PAG2 (3.0) | DRR3 | TBA (0.10) | CyHO (560) | 23.0 | 0.18 | 45 | 6.3 |
| 21 | Polymer16 (80) | PAG2 (3.0) | — | TBA (0.10) | PGMEA (480) | 31.0 | 0.16 | 38 | 3.9 |
| 22 | Polymer17 (80) | PAG2 (3.0) | — | TBA (0.10) | PGMEA (480) | 34.0 | 0.16 | 38 | 5.7 |
| 23 | Polymer18 (80) | PAG2 (3.0) | — | TBA (0.10) | PGMEA (480) | 27.0 | 0.16 | 14 | 7.0 |
| 24 | Polymer19 (80) | PAG2 (3.0) | — | AAA (0.10) | PGMEA (480) | 30.0 | 0.16 | 20 | 4.9 |
| 25 | Polymer20 (80) | PAG2 (3.0) | — | AAA (0.10) | PGMEA (480) | 25.0 | 0.17 | 30 | 3.1 |
| 26 | Polymer7 (40) Polymer10 (40) | PAG2 (3.0) | DRR4 | AACN (0.10) | CyHO (560) | 29.0 | 0.15 | 29 | 2.9 |
| 27 | Polymer7 (40) Polymer11 (40) | PAG2 (3.0) | — | TEA (0.10) | CyHO (560) | 28.0 | 0.15 | 32 | 3.4 |
| 28 | Polymer21 (80) | PAG1 (10.0) | — | TMMEA (0.10) | PGMEA (560) | 34.0 | 0.16 | 24 | 5.2 |
| 29 | Polymer21 (80) | PAG2 (5.0) | — | TMMEA (0.10) | PGMEA (560) | 50.0 | 0.15 | 23 | 4.2 |
| 30 | Polymer21 (80) | PAG3 (5.0) | — | TMMEA (0.10) | PGMEA (560) | 29.0 | 0.15 | 23 | 4.2 |

TABLE 3

| Example | Resin (part by weight) | Acid generator (part by weight) | Dissolution inhibitor or ograginc acid (part by weight) | Basic compound (part by weight) | solvent (part by weight) | Optimum exposure (mJ/cm$^2$) | Resolution (μm) | I/G bias (nm) | line-edge roughness (nm) |
|---|---|---|---|---|---|---|---|---|---|
| 31 | Polymer21 (80) | PAG3 (2.5) PAG8 (2.0) | — | TMMEA (0.10) | PGMEA/ EL (580) | 45.0 | 0.15 | 35 | 2.2 |

TABLE 3-continued

| Example | Resin (part by weight) | Acid generator (part by weight) | Dissolution inhibitor or oraganic acid (part by weight) | Basic compound (part by weight) | solvent (part by weight) | Optimum exposure (mJ/cm$^2$) | Resolution (μm) | I/G bias (nm) | line-edge roughness (nm) |
|---|---|---|---|---|---|---|---|---|---|
| 32 | Polymer21 (80) | PAG3 (2.5) PAG9 (2.0) | — | TMMEA (0.10) | PGMEA/EL (580) | 42.0 | 0.15 | 31 | 1.9 |
| 33 | Polymer21 (80) | PAG3 (2.5) PAG10 (2.0) | — | TMMEA (0.10) | PGMEA/EL (580) | 38.0 | 0.15 | 18 | 7.8 |
| 34 | Polymer22 (80) | PAG3 (5.0) | — | TMMEA (0.10) | PGMEA (560) | 39.0 | 0.15 | 21 | 2.8 |
| 35 | Polymer23 (80) | PAG3 (5.0) | — | TMMEA (0.10) | PGMEA (560) | 36.0 | 0.16 | 33 | 8.8 |
| 36 | Polymer24 (80) | PAG3 (5.0) | — | TMMEA (0.10) | PGMEA (560) | 40.0 | 0.15 | 16 | 4.1 |
| 37 | Polymer25 (80) | PAG3 (5.0) | — | TMMEA (0.10) | PGMEA (560) | 32.0 | 0.15 | 25 | 3.1 |
| 38 | Polymer26 (80) | PAG3 (5.0) | — | TMMEA (0.10) | PGMEA (560) | 29.0 | 0.16 | 24 | 6.0 |
| 39 | Polymer27 (80) | PAG3 (5.0) | — | TMEMEA (0.10) | PGMEA (560) | 48.0 | 0.16 | 30 | 3.4 |
| 40 | Polymer28 (80) | PAG3 (5.0) | — | TMEMEA (0.10) | PGMEA (560) | 19.0 | 0.15 | 22 | 3.5 |

TABLE 4

| Comp. Example | Resin (part by weight) | Acid generator (part by weight) | Dissolution inhibitor or oraginc acid (part by weight) | Basic compound (part by weight) | solvent (part by weight) | Optimum exposure (mJ/cm$^2$) | Resolution (μm) | I/G bias (nm) | line-edge roughness (nm) |
|---|---|---|---|---|---|---|---|---|---|
| 1 | Polymer1 (80) | PAG4 (8.0) | — | TBA (0.10) | PGMEA (480) | 42.0 | 0.16 | 82 | 5.1 |
| 2 | Polymer1 (80) | PAG5 (3.0) | — | TBA (0.10) | PGMEA (480) | 29.0 | 0.16 | 56 | 3.8 |
| 3 | Polymer1 (80) | PAG6 (3.0) | — | TBA (0.10) | PGMEA (480) | 33.0 | 0.16 | 102 | 4.4 |
| 4 | Polymer1 (80) | PAG4 (4.0) PAG5 (1.5) | — | TBA (0.10) | PGMEA (480) | 34.0 | 0.16 | 77 | 6.2 |
| 5 | Polymer1 (80) | PAG5 (1.5) PAG6 (1.5) | — | TBA (0.10) | PGMEA (480) | 30.0 | 0.16 | 93 | 3.8 |
| 6 | Polymer1 (80) | PAG5 (1.5) PAG7 (1.0) | — | TBA (0.10) | PGMEA (480) | 25.0 | 0.16 | 120 | 10.1 |

The invention claimed is:

1. A compound of the following general formula (1),

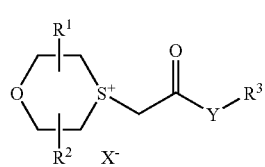

(1)

wherein:

a) $R^1$ and $R^2$ may be the same or different and each represents a hydrogen atom or a linear, branched or cyclic alkyl group having 1 to 8 carbon atoms;

b) Y represents a nitrogen atom or an alkylene group having 1 to 4 carbon atoms;

c) $R^3$ represents:

i) a linear, branched or cyclic alkyl group having 2 to 8 carbon atoms, an aryl group having 6 to 16 carbon atoms, and may be substituted by an alkyl group having 1 to 4 carbon atoms, a fluorinated alkyl group having 1 to 4 carbon atoms, an alkoxy group having 1 to 4 carbon atoms, a fluorinated alkoxy group having 1 to 4 carbon atoms, a nitro group, a cyano group, a fluorine atom, a phenyl group, a substituted phenyl group, an acetyl group or a benzoyloxy group when Y represents an alkylene group having 1 to 4 carbon atoms, or ii) a linear, branched or cyclic alkyl group having 1 to 8 carbon atoms, an aryl group having 6 to 16 carbon atoms, and may be substituted by an alkyl group having 1 to 4 carbon atoms, a fluorinated alkyl group having 1 to 4 carbon atoms, an alkoxy group having 1 to 4 carbon atoms, a fluorinated alkoxy group having 1 to 4 carbon atoms, a nitro group, a cyano group, a fluorine atom, a phenyl group, a substituted phenyl group, an acetyl group or a benzoyloxy group when Y represents a nitrogen atom; and d) $X^-$ represents a non-nucleophilic counter ion having 1 to 20 carbon atoms.

2. The compound according to claim 1 wherein both $R^1$ and $R^2$ are a hydrogen atom in the general formula (1).

3. The compound according to claim 1 wherein $R^3$ represents a phenyl group or a naphthyl group in the general formula (1).

4. The compound according to claim 2 wherein $R^3$ represents a phenyl group or a naphthyl group in the general formula (1).

5. A positive resist material comprising a photo acid generator which is said compound according to claim 1 and a base resin in which a hydrogen atom of a carboxyl group or a hydrogen atom of a phenolic hydroxyl group is substituted by an acid-labile group having an alkali dissolution controlling ability wherein the acid-labile group is dissociated by an action of an acid generated in light exposure so that solubility of the base resin in an alkali aqueous solution will increase.

6. The positive resist material according to claim 5 wherein said base resin is one or more polymers partially substituted by the acid-labile group having the alkali dissolution controlling ability, said one or more polymers being selected from the group consisting of polyhydroxystyrene and derivatives thereof, polyacrylic acid and derivatives thereof, polymethacrylic acid and derivatives thereof; copolymers formed by monomers from hydroxystyrene, acrylic acid, methacrylic acid and derivatives thereof; copolymers formed by three or more monomers selected from cycloolefins and derivatives thereof, maleic anhydride, acrylic acid and derivatives thereof; copolymers formed by three or more monomers selected from cycloolefins and derivatives thereof, maleimide, acrylic acid and derivatives thereof; polynorbornene; and metathesis polymers by ring-opening polymerizaion.

7. The positive resist material according to claim 5 wherein said base resin is of a polymer structure containing a silicon atom.

8. The positive resist material according to claim 5, further comprising a basic compound.

9. The positive resist material according to claim 5, further comprising a dissolution inhibitor.

10. The positive resist material according to claim 8, further comprising a dissolution inhibitor.

11. A pattern formation method comprising the steps of applying the positive resist material according to claim 5 on a substrate, then heat-treating the material, exposing the treated material to a high energy ray having a wavelength of 300 nm or less via a photo mask, optionally heat-treating the exposed material, and developing the material using a developer.

12. A pattern formation method comprising the steps of applying the positive resist material according to claim 8 on a substrate, then heat-treating the material, exposing the treated material to a high energy ray having a wavelength of 300 nm or less via a photo mask, optionally heat-treating the exposed material, and developing the material using a developer.

13. A pattern formation method comprising the steps of applying the positive resist material according to claim 9 on a substrate, then heat-treating the material, exposing the treated material to a high energy ray having a wavelength of 300 nm or less via a photo mask, optionally heat-treating the exposed material, and developing the material using a developer.

14. A pattern formation method comprising the steps of applying the positive resist material according to claim 10 on a substrate, then heat-treating the material, exposing the treated material to a high energy ray having a wavelength of 300 nm or less via a photo mask, optionally heat-treating the exposed material, and developing the material using a developer.

15. A compound selected from one of the following:

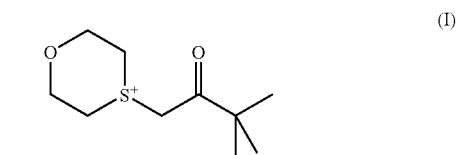

(I)

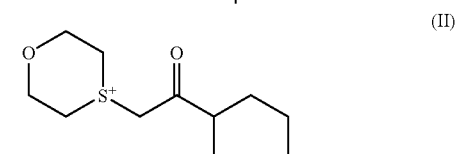

(II)

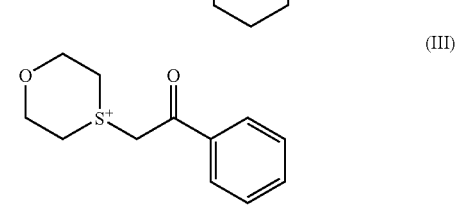

(III)

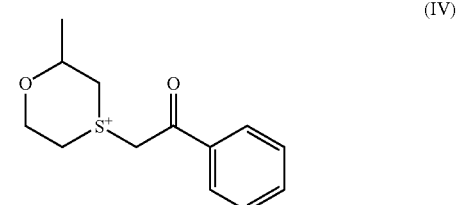

(IV)

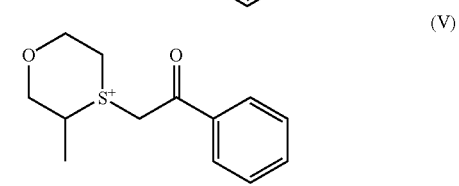

(V)

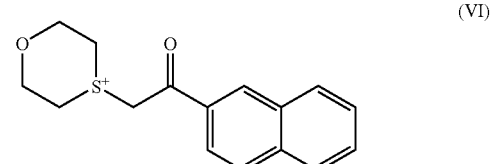

(VI)

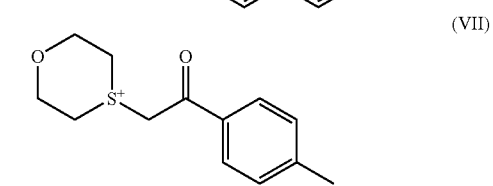

(VII)

-continued
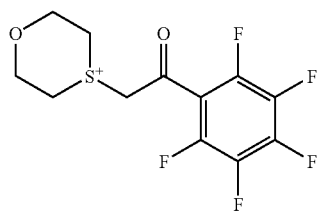
(VIII)
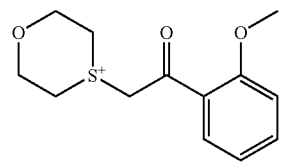
(IX)
-continued
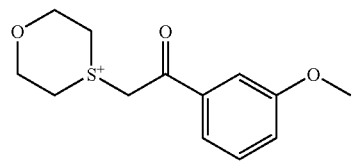
(X)
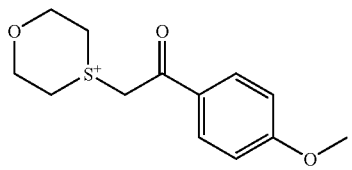
(XI)
and a non-nucleophilic counter ion having 1 to 20 carbon atoms.
* * * * *